(12) United States Patent
Huynh et al.

(10) Patent No.: US 6,945,997 B2
(45) Date of Patent: *Sep. 20, 2005

(54) HEART VALVES AND SUTURE RINGS THEREFOR

(75) Inventors: Van Le Huynh, Tustin, CA (US); Than Nguyen, Anaheim, CA (US); Hung Ly Lam, Norco, CA (US); Xiaoming G. Guo, Dove Canyon, CA (US); Ralph Kafesjian, Newport Beach, CA (US)

(73) Assignee: Edwards Lifesciences Corporation, Irvine, CA (US)

(*) Notice: Subject to any disclaimer, the term of this patent is extended or adjusted under 35 U.S.C. 154(b) by 127 days.

This patent is subject to a terminal disclaimer.

(21) Appl. No.: 10/412,160

(22) Filed: Apr. 11, 2003

(65) Prior Publication Data

US 2003/0195620 A1 Oct. 16, 2003

Related U.S. Application Data

(60) Continuation of application No. 09/599,200, filed on Jun. 22, 2000, now Pat. No. 6,585,766, which is a division of application No. 09/264,801, filed on Mar. 9, 1999, now Pat. No. 6,102,944, which is a division of application No. 08/826,408, filed on Mar. 27, 1997, now Pat. No. 5,928,281.

(51) Int. Cl.[7] .................................................. A61F 2/24
(52) U.S. Cl. ..................................... 623/2.17; 623/2.41
(58) Field of Search ................................ 623/FOR 101, 623/2.38–2.41, 900, 2.12–2.19

(56) References Cited

U.S. PATENT DOCUMENTS

| | | | |
|---|---|---|---|
| 4,035,849 A | | 7/1977 | Angell et al. |
| 4,535,483 A | * | 8/1985 | Klawitter et al. ............ 623/2.4 |
| 5,032,128 A | | 7/1991 | Alonso |
| 5,549,665 A | | 8/1996 | Vesely et al. |
| 5,755,782 A | | 5/1998 | Love et al. |
| 5,766,240 A | | 6/1998 | Johnson |

FOREIGN PATENT DOCUMENTS

| | | |
|---|---|---|
| SU | 1116573 A | 7/1985 |
| WO | WO 92/13502 | 8/1992 |
| WO | WO 92/19184 | 11/1992 |
| WO | WO 95/28899 | 11/1995 |

* cited by examiner

Primary Examiner—David H. Willse
(74) Attorney, Agent, or Firm—John C. James; Rajiv Yadav; Guy L. Cumberbatch

(57) ABSTRACT

Improved, adaptable tissue-type heart valves and methods for their manufacture are disclosed wherein a dimensionally stable, pre-aligned tissue leaflet subassembly is formed and its peripheral edge clamped between and attached to an upper shaped wireform and a lower support stent. A variety of adaptable structural interfaces including suture rings, flanges, and conduits may be attached to the support stent with or without an outlet conduit disposed about the wireform to provide a tissue-type heart valve adaptable for use in either a natural heart or in mechanical pumping devices. The methods include forming individual leaflets with a template and using the template to attach the leaflets together to form a tissue leaflet subassembly. The template and leaflets include a straight edge terminating in oppositely directed tabs, and a curvilinear cusp edge extending opposite the straight edge. The template may include a guide slot in its straight edge and the assembly includes aligning two leaflet tabs with the template and passing sutures through the guide slot and through the leaflet tabs. The leaflet subassembly is mated to a wireform with the tabs extending through commissure posts of the wireform. A support stent having an upper surface matching the lower surface of the wireform sandwiches the edges of the leaflet subassembly therebetween. Separated tabs on the leaflet subassembly are passed through the wireform commissures and attached to adjacent stent commissures so as to induce clamping of the leaflet tabs between the stent commissures and wireform commissures upon a radially inward force being applied to the leaflets.

13 Claims, 16 Drawing Sheets

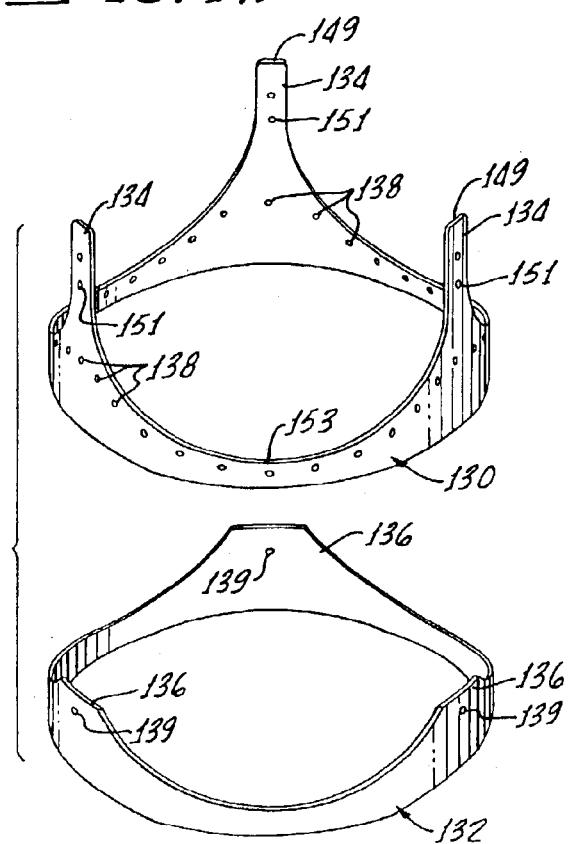
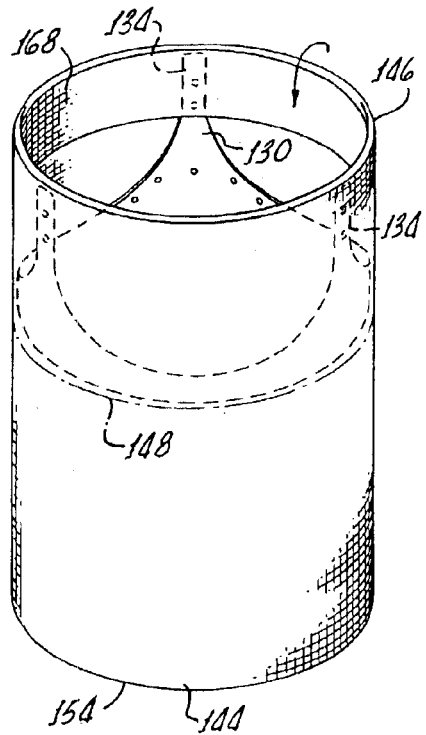
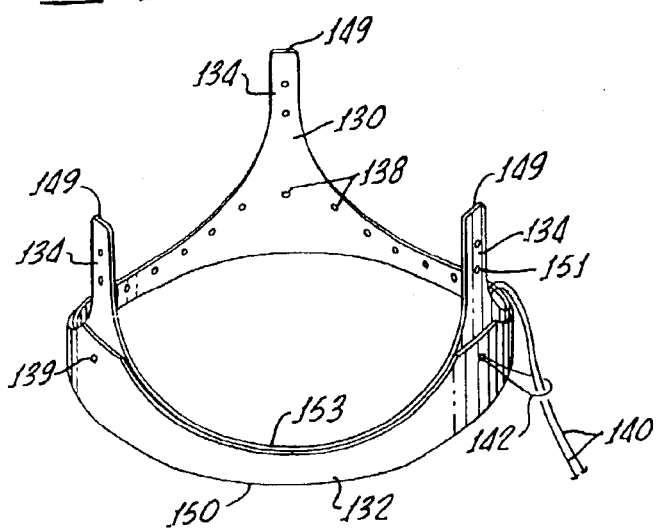

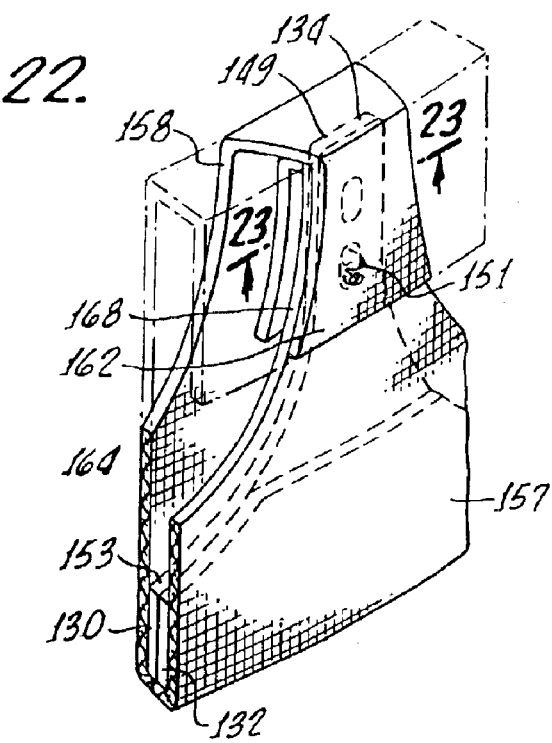
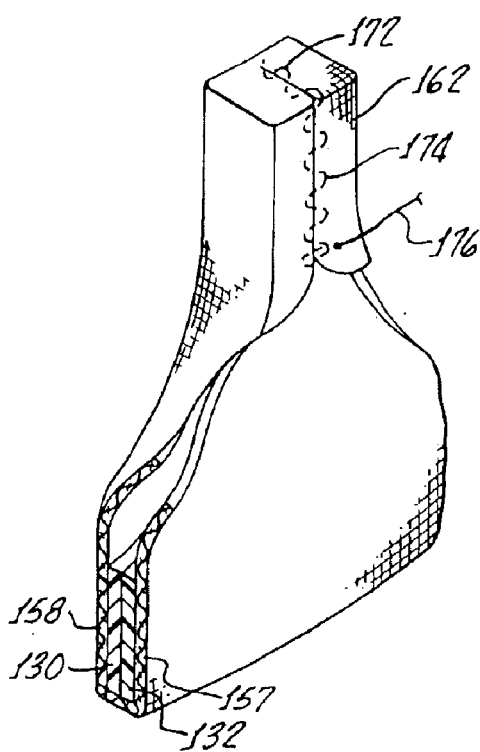
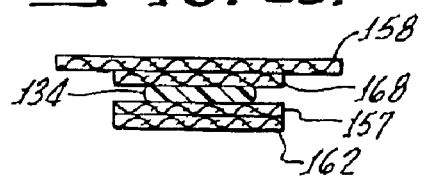
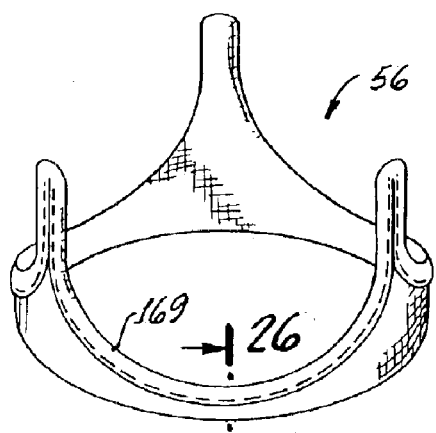
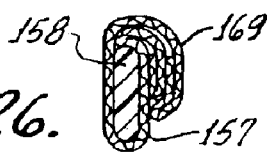

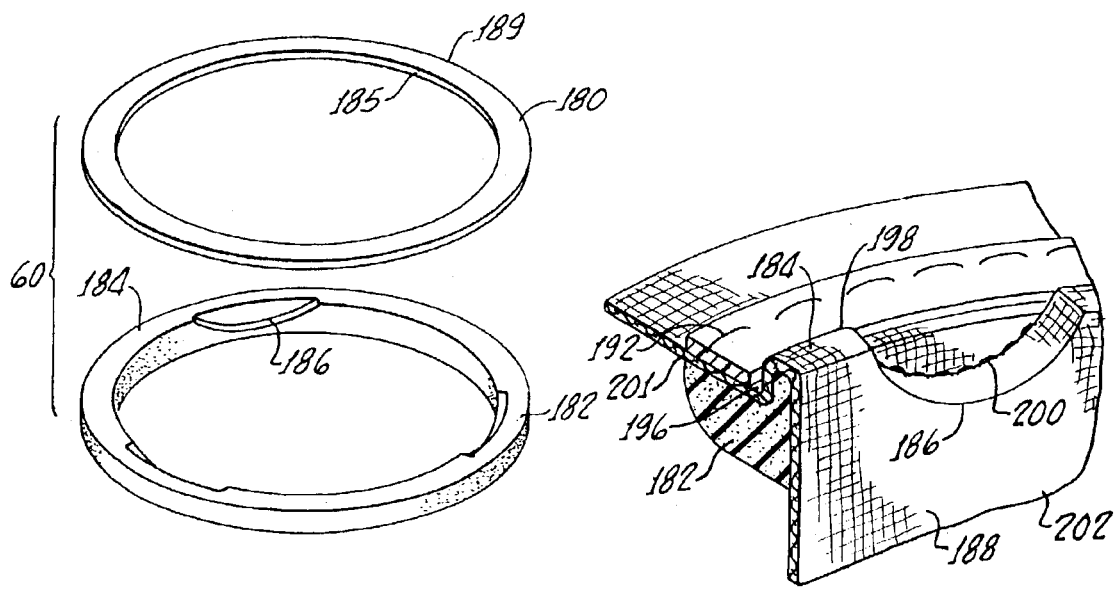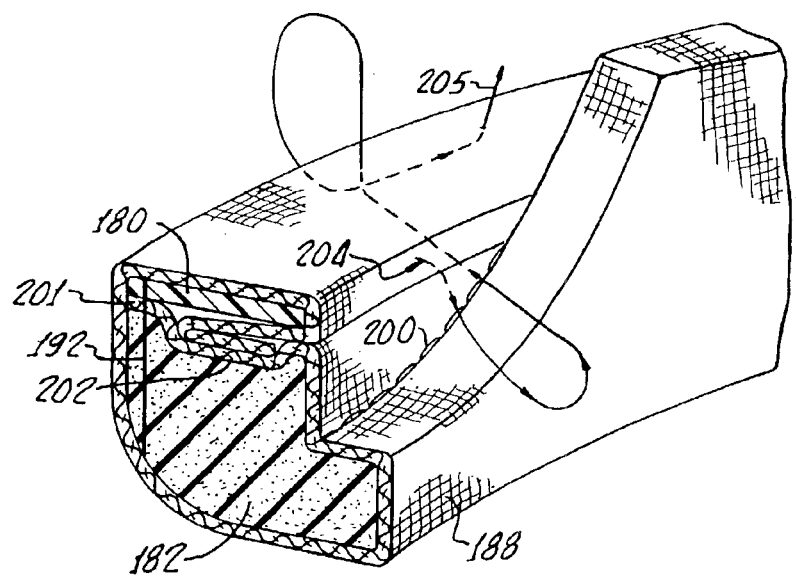

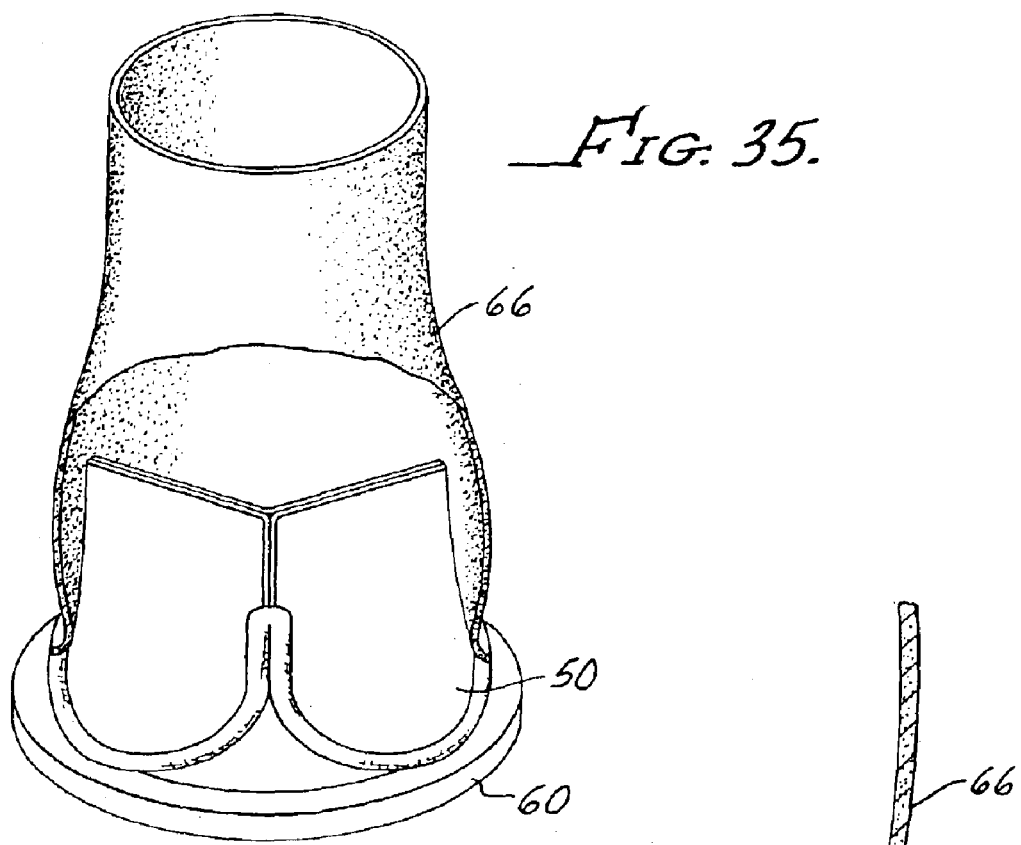
FIG. 35.
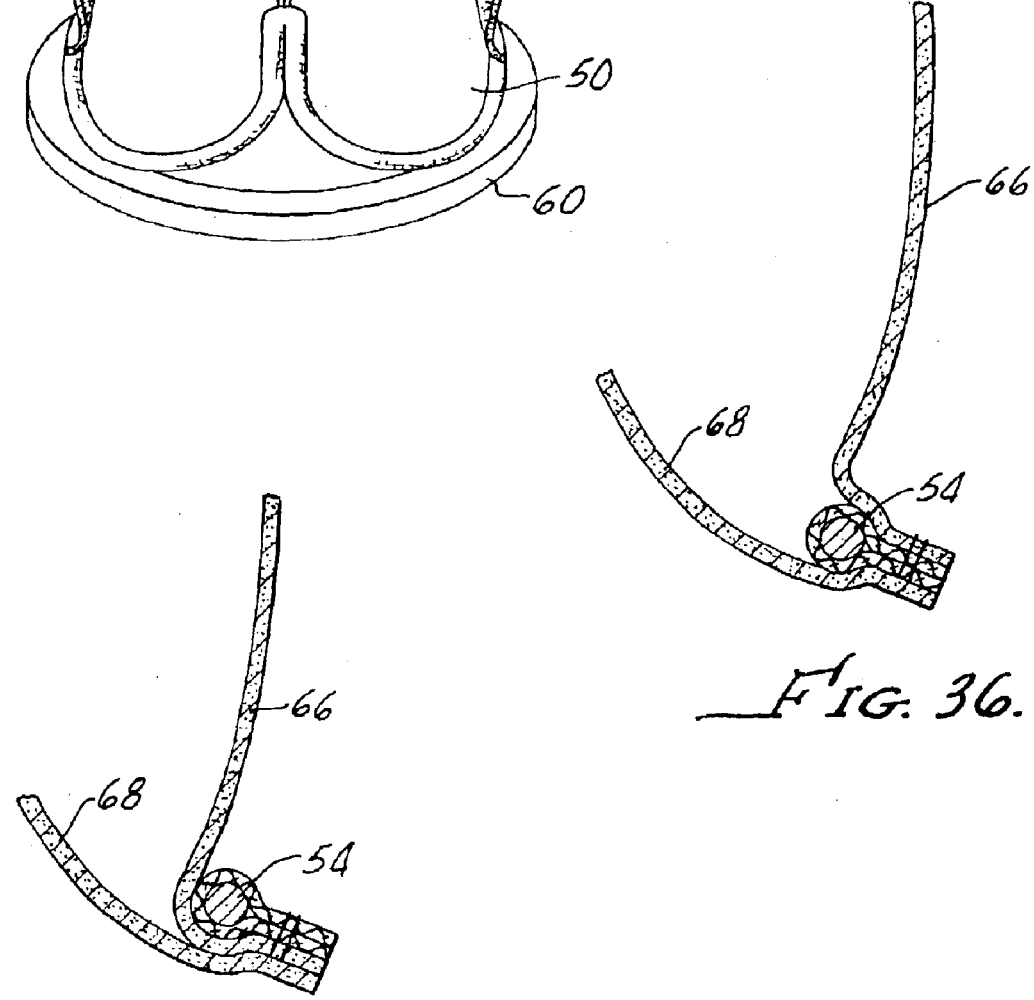
FIG. 36.
FIG. 37.

HEART VALVES AND SUTURE RINGS THEREFOR

RELATED APPLICATIONS

The present application is a continuation of U.S. application Ser. No. 09/599,200, filed Jun. 22, 2000 now U.S. Pat. No. 6,585,766, entitled "Cloth-Covered Stents for Tissue Heart Valves," which is a division of U.S. application Ser. No. 09/264,801, filed Mar. 9, 1999, entitled "Methods of Tissue Heart Assembly," now issued as U.S. Pat. No. 6,102,944, which is a divisional of U.S. application Ser. No. 08/826,408, filed Mar. 27, 1997, entitled "Tissue Heart Valves with Subassemblies," now issued as U.S. Pat. No. 5,928,281.

FIELD OF THE INVENTION

The present invention is directed to prosthetic heart valves and in particular to valves having suture rings and the suture rings themselves.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves. Two primary types of heart valve replacements or prostheses are known. One is a mechanical-type heart valve that uses a pivoting mechanical closure to provide unidirectional blood flow. The other is a tissue-type or "bioprosthetic" valve which is constructed with natural-tissue valve leaflets which function much like a natural human heart valve, imitating the natural action of the flexible heart valve leaflets which seal against each other or coapt between adjacent tissue junctions known as commissures. Each type of prosthetic valve has its own attendant advantages and drawbacks.

Operating much like a rigid mechanical check valve, mechanical heart valves are robust and long lived but require that valve implant patients utilize blood thinners for the rest of their lives to prevent clotting. They also generate a clicking noise when the mechanical closure seats against the associated valve structure at each beat of the heart. In contrast, tissue-type valve leaflets are flexible, silent, and do not require the use of blood thinners. However, naturally occurring processes within the human body may attack and stiffen or "calcify" the tissue leaflets of the valve over time, particularly at high-stress areas of the valve such as at the commissure junctions between the valve leaflets and at the peripheral leaflet attachment points or "cusps" at the outer edge of each leaflet. Further, the valves are subject to stresses from constant mechanical operation within the body. Accordingly, the valves wear out over time and need to be replaced. Tissue-type heart valves are also considerably more difficult and time consuming to manufacture.

Though both mechanical-type and tissue-type heart valves must be manufactured to exacting standards and tolerances in order to function for years within the dynamic environment of a living patient's heart, mechanical-type replacement valves can be mass produced by utilizing mechanized processes and standardized parts. In contrast, highly trained and skilled assembly workers make tissue-type prosthetic valves by hand. Typically, tissue-type prosthetic valves are constructed by sewing two or three flexible natural tissue leaflets to a generally circular supporting wire frame or stent. The wire frame or stent is constructed to provide a dimensionally stable support structure for the valve leaflets which imparts a certain degree of controlled flexibility to reduce stress on the leaflet tissue during valve closure. A biocompatible cloth covering on the wire frame or stent provides sewing attachment points for the leaflet commissures and cusps. Similarly, a cloth covered suture ring can be attached to the wire frame or stent to provide an attachment site for sewing the valve structure in position within the patient's heart during a surgical valve replacement procedure.

With over fifteen years of clinical experience supporting their utilization, tissue-type prosthetic heart valves have proven to be an unqualified success. Recently their use has been proposed in conjunction with mechanical artificial hearts and mechanical left ventricular assist devices (LVADs) in order to reduce damage to blood cells and the associated risk of clotting without using blood thinners. Accordingly, a need is developing for a tissue-type prosthetic heart valve that can be adapted for use in conjunction with such mechanical pumping systems. This developing need for adaptability has highlighted one of the drawbacks associated with tissue-type valves—namely, the time consuming and laborious hand-made assembly process. In order to provide consistent, high-quality tissue-type heart valves having stable, functional valve leaflets, highly skilled and highly experienced assembly personnel must meticulously wrap and sew each leaflet and valve component into an approved, dimensionally appropriate valve assembly. Because of variations in tissue thickness, compliance and stitching, each completed valve assembly must be fine tuned using additional hand-crafted techniques to ensure proper coaptation and functional longevity of the valve leaflets. As a result, new challenges are being placed upon the manufacturers of tissue-type prosthetic valves in order to meet the increasing demand and the increasing range of uses for these invaluable devices.

Accordingly, consistent with the developing practice of the medical profession, there is a continuing need for improved tissue-type prosthetic heart valves which incorporate the lessons learned in clinical experience, particularly the reduction of stress on the valve leaflets while maintaining desirable structural and functional features. Additionally, there is a growing need for improved tissue-type prosthetic heart valves which can be adapted for use in a variety of positions within the natural heart or in mechanical pumps, such as artificial hearts or ventricular assist devices, as well as alternative locations in the circulatory system. Further, in order to address growing demand for these devices, there is a need for tissue-type heart valves that are simpler and easier to manufacture in a more consistent manner than are existing valves.

SUMMARY OF THE INVENTION

Directed to achieving the foregoing objective and to remedying the problems in the prior art, disclosed herein are novel tissue heart valve constructions and components thereof, and simplified methods of fabricating the same. The improved tissue heart valves of the present invention are fabricated to include standardized leaflet structure subassemblies that can be modified readily to adapt to different intended applications. Of equal importance, the leaflet structure subassemblies uniformly distribute tensile loads along the entire peripheral leaflet cusp, reducing stress points and significantly improving the long-term functionality of the valve assembly. As an added benefit of the present invention, the stability and adaptability of the tissue valve subassembly is achieved through simplified manufacturing processes utilizing fewer steps and subassemblies. This manufacturing protocol can be incorporated into branched, adaptable manufacturing techniques for the production of tissue heart valves having a variety of end uses. Further, these improved construction techniques expedite the overall manufacturing process and improve the consistency of the tissue valves so produced while simultaneously reducing the need for post-assembly fine tuning and quality-control procedures.

According to one aspect of the present invention, a tissue-type heart valve includes a dimensionally stable, pre-aligned tissue leaflet subassembly, a generally circular wireform, and a generally circular support stent. The wireform has a bottom surface dimensioned to receive the pre-aligned tissue leaflet subassembly in fixed, mating engagement. The support stent has an upper surface dimensioned to seat and fix in meeting engagement with the pre-aligned tissue leaflet subassembly which is fixedly disposed in mating engagement with the bottom surface of the wireform.

Pursuant to this construction, an exemplary tissue valve includes a plurality of tissue leaflets that are templated and attached together at their tips to form a dimensionally stable and dimensionally consistent coapting leaflet subassembly. Then, in what is essentially a single process, each of the leaflets of the subassembly is aligned with and individually sewn to a cloth-covered wireform, from the tip of one wireform commissure uniformly, around the leaflet cusp perimeter, to the tip of an adjacent wireform commissure. As a result, the sewed sutures act like similarly aligned staples, all of which equally take the loading force acting along the entire cusp of each of the pre-aligned, coapting leaflets. The resulting tissue-wireform structural assembly thereby formed reduces stress and potential fatigue at the leaflet suture interface by distributing stress evenly over the entire leaflet cusp from commissure to commissure. This improved, dimensionally stable, reduced-stress assembly is operatively attached to the top of a previously prepared cloth-covered stent to clamp the tissue leaflet cusps on a load-distributing cloth seat formed by the top of the cloth-covered stent without distorting the leaflets or disturbing their relative alignment and the resultant coaptation of their mating edges.

The stent is secured to the assembly with the commissures of the stent extending up into the corresponding commissures of the leaflet, wireform assembly. The stent itself can be formed of an inner polyester film support secured to a surgically acceptable metal ring such as an Elgiloy™ metal stiffener having a cloth cover cut, folded and sewn around the support and stiffener combination. Alternatively, instead of having an Elgiloy outer band and a laminated polyester film support, the two stent layers can both be polyester layers or a single piece stent having appropriately flexible commissure posts. Either stent construction provides support and dimensional stability for the valve structure extending from commissure to commissure and being evenly distributed around each leaflet. This assembly methodology allows the evenly sutured tissue of the leaflet cusps to be sandwiched between the wireform and the stent and to thereby further distribute the loading forces more evenly around the attachment site. Because the tissue leaflets experience lower, more evenly distributed stresses during operation, they are less likely to experience distortion in use. Thus, a more stable, long lived, functional closure or coaptation of the leaflets is provided by this even distribution of attachment forces.

A number of additional advantages result from the present invention and the stent construction utilized therein. For example, for each key area of the stent, the flexibility can be optimized or customized. If desired, the coapting tissue leaflet commissures can be made more or less flexible to allow for more or less deflection to relieve stresses on the tissue at closing or to fine tune the operation of the valve. Similarly, the base radial stiffness of the overall valve structure can be increased or decreased to preserve the roundness and shape of the valve.

Unlike a rigid mechanical valve, the stent does not act as a rigid heart valve structure but as a radially stable, yet axially flexible support. A rigid structure is unnecessary by utilizing the teachings of the present invention because the valve leaflets are dimensionally pre-aligned along their mutually coapting mating or sealing edges prior to being directly attached to the base of the cloth-covered wireform. As a result, the entire sealing aspect of the valve can be aligned in three dimensions at once without the variability previously experienced in the construction of prior art tissue-type valves. In addition to eliminating the need for post-assembly adjustment, this pre-alignment provides for consistency and simplicity in the manufacture of the valve structure. Further, the wireform functions as a template for suturing the leaflet cusps to the valve subassembly with uniform stitching from commissure tip to commissure tip. This produces a dimensionally consistent structure that can interface with the stent in a previously unobtainable uniform manner. The consistent dimensional integrity of the leaflet wireform subassembly enables the stent to function as a stress relieving support clamp which further secures the leaflet cusps in the valve structure to provide an added degree of stability and stress distribution. If desired, providing the top of the stent with a single or double fold of covering cloth provides the stent lip with a deformable cloth seat that assists in the distribution of load around the leaflet cusps and simplifies sewing the stent to the tissue leaflet wireform subassembly. Those skilled in the art will appreciate that attaching the stent to the tissue leaflet wireform functions to stabilize the projecting commissure posts of the valve subassembly without stiffening their desirable axial flexibility. This novel construction technique eliminates the need for separate commissure posts at the tissue leaflet commissures and also eliminates multiple tissue and cloth layers at the wireform commissure posts which adds to uniformity and consistency in valve production and eliminates assembly steps. As a result, valve manufacture is not only improved, but also simplified and expedited as well.

The stent also functions as an adaptable structural interface, allowing the tissue-wireform-stent structural subassembly to be attached to a variety of additional structures dependent upon intended valve placement and operating environments. For example, with the supporting stent secured to the tissue-wireform structural assembly, the resulting valve assembly can be attached to, for example, a suture ring, a flange or a conduit depending on the desired valve application. To form a conduit valve, the suture ring can be attached directly to the inflow or base of the stent to enable the implanting surgeon to sew the valve in place within the heart. Alternatively, when the valve is to be used for artificial hearts or for left ventricular assist devices (LVADs), a more rigid flange can be attached to the stent inflow to function as a mechanical mount. In some circumstances it may be desirable to form a conduit valve wherein flexible or rigid conduits are required to replace a missing portion of a patient's aorta or to interface with an artificial blood pumping device. In such circumstances, an inlet conduit may be attached to the stent inflow and, if desired, a corresponding outflow conduit can be attached inside or outside of the valve wireform. Unlike prior art tissue heart valves, the present invention provides this flexibility and adaptability of use because key valve components can be standardized for different types of valves or valve applications. This manufacturing and structural consistency also improves quality control and provides repeatability and consistency in the formation of the valves. It also simplifies final assembly that in turn provides for increased production rates without sacrificing consistent product quality.

More specifically, as part of the flexibility of the present invention, the stent is designed to be adaptable so that different ways of attaching the valve to its various intended applications can be accommodated. The novel construction that allows for this universal application results from the stent providing a complete uniform support to the dimensionally stable, pre-aligned wireform/leaflet subassembly. Because of this adaptability, the valve of the present invention can function in a variety of applications, including that of a temporary heart valve prosthesis within a circulatory support system using a relatively rigid flange or a conduit assembly rather than a standard soft sewing ring. Alternatively, the present invention can function as a prosthetic valve having a soft, scallop-shaped sewing ring for aortic positioning or a soft flat sewing ring for mitral positioning, or as a conduit valve by incorporating proximal and distal conduits attached on both the inflow and outflow valve ends. The outflow conduit can have a sinus shape to improve blood flow if desired. Within an artificial heart system, the valve of the present invention mimics the hemodynamic pumping action of the heart while sustaining the patient until a donor heart is located and successfully transplanted. In this application, both blood inflow and outflow functions can be accommodated by the present invention.

Other objects and advantages of the present invention will become more apparent to those persons having ordinary skill in the art to which the present invention pertains from the following description taken in conjunction with the accompanying drawings.

BRIEF DESCRIPTION OF THE DRAWINGS

FIG. 17 is an exploded perspective view illustrating an exemplary multi-piece stent formed of a flexible support and an associated stiffener of the present invention;

FIG. 18 is a perspective view illustrating the attachment of the support to the stiffener of FIG. 17;

FIG. 19 is a perspective view illustrating an initial step in the covering of the stent components of FIG. 18 with cloth;

FIG. 22 is an enlarged view of a portion of FIG. 20 illustrating subsequent fabrication steps;

FIG. 23 is an enlarged cross-sectional view taken on line 23—23 of FIG. 22;

FIG. 24 is a view similar to FIG. 22 illustrating additional fabrication steps;

FIG. 25 is a perspective view of the cloth-covered stent of FIG. 18 illustrating the cloth seating lip;

FIG. 26 is an enlarged cross-sectional view on line 26—26 of FIG. 25 illustrating additional aspects of the fabrication of the exemplary stent assembly;

FIG. 27 is a perspective view illustrating initial components of an exemplary suture ring of the present invention;

FIG. 30 is an enlarged sectional view of a portion of FIG. 29 illustrating additional aspects of the fabrication of the suture ring assembly;

FIG. 31 is an enlarged sectional view illustrating additional aspects of the finished exemplary suture ring assembly;

FIG. 35 is a cutaway perspective view illustrating an exemplary attachment of an outflow conduit to an exemplary valve of the present invention;

FIG. 36 is an enlarged cross-sectional view illustrating additional aspects of the conduit attachment;

FIG. 37 is a cross sectional view similar to FIG. 36 illustrating alternative conduit attachment features.

DETAILED DESCRIPTION OF EXEMPLARY EMBODIMENTS

Figure 1:
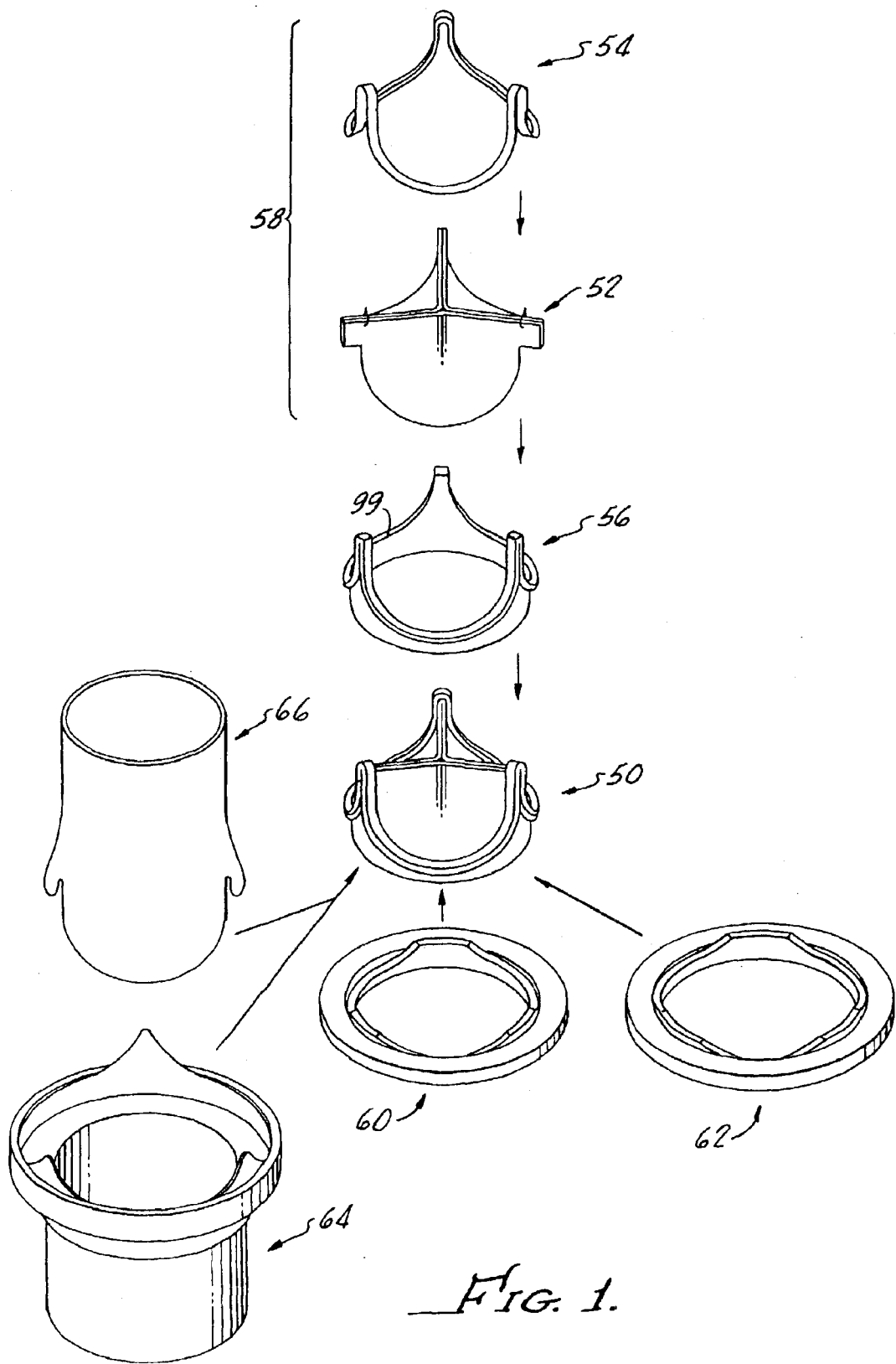
FIG. 1 is an exploded perspective view of an exemplary heart valve of the present invention illustrating the assembly relationship of the standardized components and alternative valve attachment application structures.

Referring more particularly to the drawings, FIG. 1 is an exploded assembly view, illustrating exemplary alternative embodiments of an improved, adaptable tissue valve 50, its individual components, and its alternative configurations produced in accordance with the teachings of the present invention. Valve 50 includes a pre-aligned, standardized leaflet subassembly 52, a cloth-covered wireform 54 and a support stent 56. As will be discussed in detail below, during assembly of valve 50, the pre-aligned leaflet subassembly 52 and the cloth-covered wireform 54 are first assembled in accordance with the present invention to form a tissue-wireform structural assembly 58 (see FIGS. 2 to 9). Then, the structural assembly 58 is secured to stent 56 to form the assembled valve 50.

As illustrated FIG. 1, valve 50 is uniquely configured to enable production of several useful alternative valves for a variety of end-use applications. For example, if the desired application is the replacement of a native heart valve, valve 50 can be attached to a relatively soft suture ring 60 for subsequent sewing into place within a heart (not shown). Alternatively, if it is desired to use valve 50 in a left ventricular assist device (LVAD) or in a mechanical heart pump, valve 50 can be mounted to an appropriately rigid mechanical flange 62. Further, in both natural and mechanical applications where it is desirable to incorporate a conduit, valve 50 may be attached to either an inflow conduit 64 and/or an outflow conduit 66.

Production of the Tissue-Wireform Structural Assembly

In the present disclosure, exemplary valve 50 is illustrated as a three-leaflet or tricuspid valve. However, it will be appreciated by those skilled in the art that valve 50 may be configured to have two leaflets or any other desired leaflet configuration depending on the intended application.

A first step in the assembly of tissue valve 50 is the attachment of tissue leaflets 68 to one another to form a consistently dimensioned, standardized leaflet subassembly. Tissue leaflets are typically formed from pericardial, porcine or similar tissue obtained from donor organs, which tissue is preserved or "fixed" prior to use in assembling a valve. Those skilled in the art will appreciate that the dimensions of leaflet subassembly 52 will vary depending upon the intended end use and associated positioning and dimensional requirements of the finished valve. However, pre-alignment and stitching in accordance with the teachings of the present invention not only simplifies the manufacture of valve 50 but also functions to align the entire valve mating or seating surfaces at once. This eliminates variations in leaflet alignment and dimensional relationships and significantly minimizes the need to adjust the tissue leaflets after final assembly of the valve in order to ensure proper coaptation at the mating edges of the leaflets.

Figure 2:
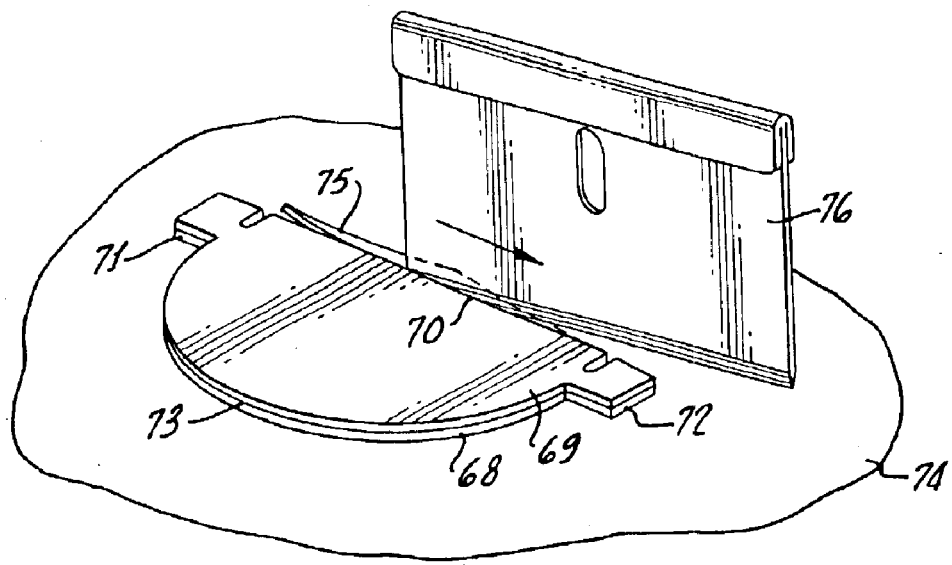
FIG. 2 is a perspective view illustrating the step of templating and trimming exemplary leaflets used in making a tissue heart valve of the present invention.

Referring now to FIG. 2, the desired number of tissue leaflets 68 (in this example, three leaflets) are obtained from natural tissue as known in the art, and each leaflet 68 is trimmed to the appropriate desired shape and size for the intended valve use using template 69, defining a generally straight or linear coapting mating edge 70 having opposing ends 71, 72 and a generally arcuate peripheral cusp 73 extending therebetween. More particularly, each leaflet 68 is placed on a cutting board 74 and the selected template 69 is then placed over the leaflet 68. Tissue 75 extending beyond the boundaries of template 69 is then cut away using a sharp razor blade 76 or similar cutting tool.

Figure 3:
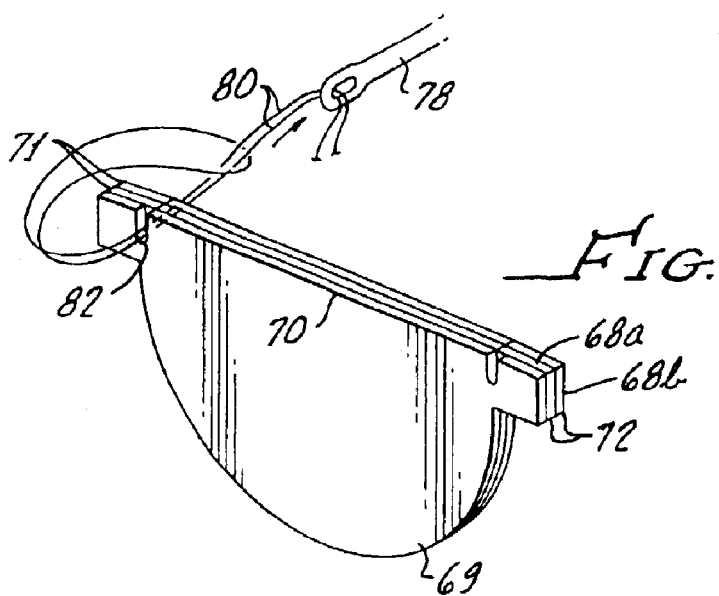
FIG. 3 illustrates the initial steps of templating and pre-aligning the leaflets of the valve subassembly.

A characteristic of pericardial tissue is that one surface is smoother than the opposite surface. Accordingly, it is desirable that the less smooth surface be identified to serve as the mating surface at edge 70 with an adjacent leaflet edge 70. After the leaflets 68 are trimmed and the mating surfaces identified, two of the leaflets 68a, 68b are pre-aligned or mated together along with template 69 as shown in FIG. 3. The two leaflets 68a, 68b are then attached or stitched together at one end 71 to define the first in a plurality of pairs of aligned, mating leaflet ends. For example, a needle that has-been "double-threaded," that is, needle 78 that has been threaded with a looped (or "folded") segment of thread 80 is inserted and pushed through the leaflets 68a, 68b at the location dictated by guide slot 82 at one end of template 69. Template 69 may then be removed, with needle 78 being brought over the top of leaflets 68a, 68b and passed back through the loop and pulled tightly. Naturally, alternative attachment methods or stitches may be utilized within the scope and teaching of the present invention. The opposite ends 72 of the first two leaflets 68a, 68b of the exemplary three leaflet valve are not sewn together at this time.

Figure 4:
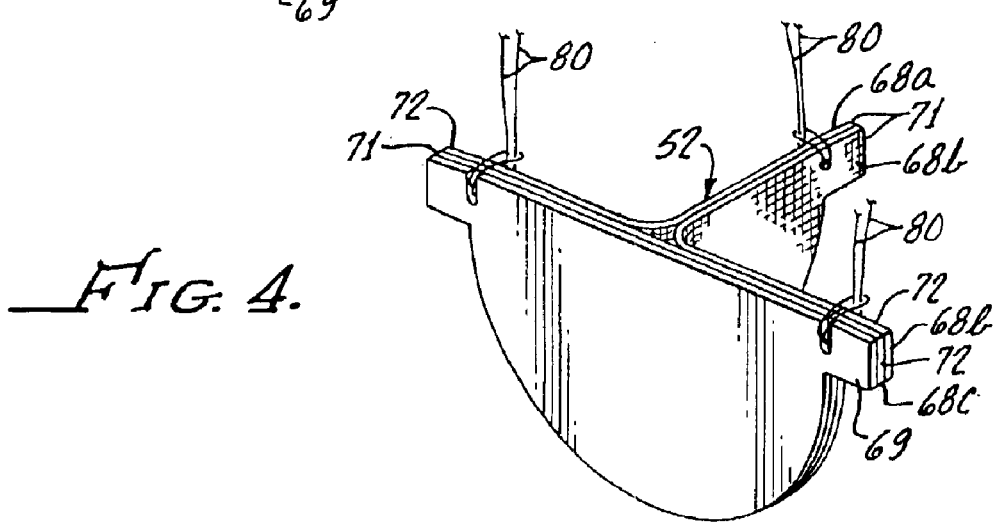
FIG. 4 shows additional steps in the pre-alignment of the valve leaflet subassembly.

Referring now to FIG. 4, a third leaflet 68c is pre-aligned and attached to the other two leaflets 68a, 68b in a tricuspid format, again using template 69. In particular, third leaflet 68c is mated with template 69, and the respective unsewn ends 72 of the first two leaflets 68a, 68b are spread out and then aligned with the respective opposite ends 71, 72 of templated third leaflet 68c. Again using guide slot 82 of the template 69 as a guide, a double-threaded needle with thread 80 is inserted through each of the unsewn pairs of the three leaflets 68a, 68b, 68c to secure the leaflet ends together in pairs as shown. The template may then be removed, and, for each stitch, needle 78 may be brought over the top of leaflets 68a, 68b, 68c and passed back through the loop and pulled tightly to produce leaflet subassembly 52 having three leaflet mating ends.

Figure 5:
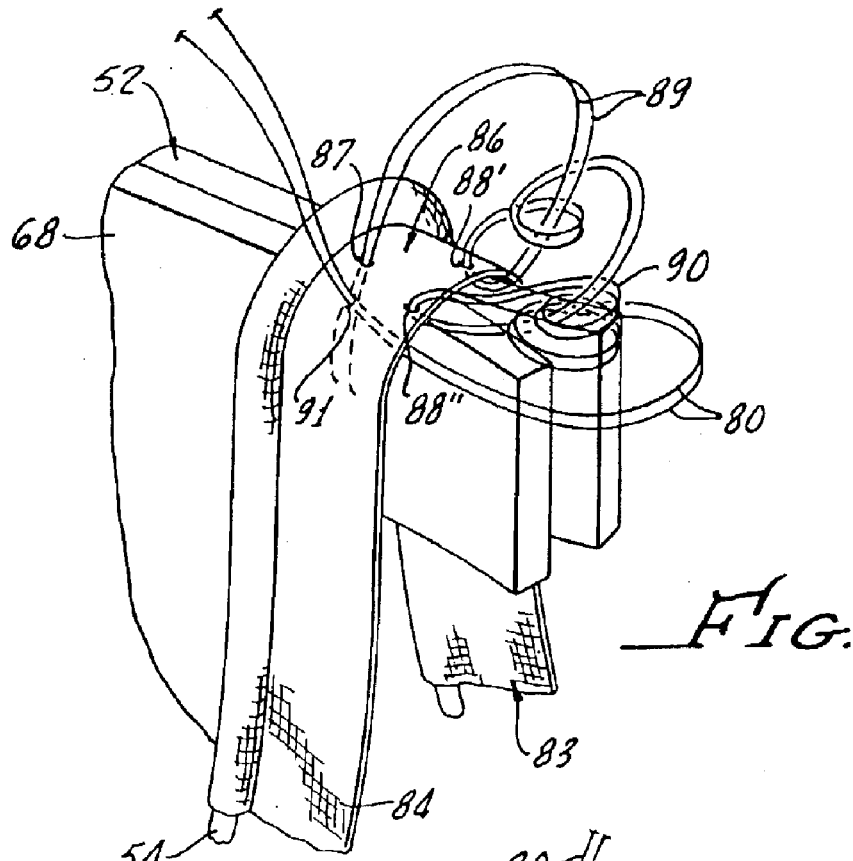
FIG. 5 is an enlarged view illustrating an exemplary attachment step of the pre-aligned leaflets to a wireform commissure tip.
Figure 6:
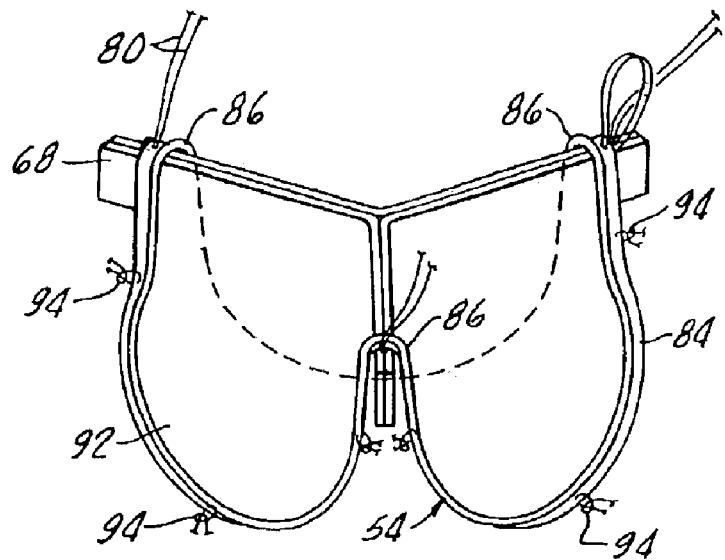
FIG. 6 is a perspective view illustrating the subsequent preliminary attachment of the exemplary leaflet cusps to the wireform of FIG. 5.

Referring now to FIGS. 5 and 6, it is preferred to attach leaflet subassembly 52 to the underside or bottom 83 of wireform 54. Exemplary wireform 54 is a wire reinforced cloth having a cloth edge 84 and is shaped in a manner substantially conforming to the shape of the leaflet subassembly structure 52. In the embodiment shown, wireform 54 is generally circular in shape and has a sinusoidal undulation defining a plurality of commissure tips 86 corresponding to the pairs of leaflet mating ends. The cloth of wireform 54 includes the circumferential cloth edge 84 that serves as a sewing or attachment surface for the leaflet subassembly 52. Exemplary wireform 54 includes the three raised commissure tips 86 which receive the three respective pairs of attached mating ends of leaflets 68a, b, and c of the pre-aligned leaflet subassembly 52.

An exemplary technique for attaching the leaflet pairs at an end of the leaflet subassembly 52 to one of the commissure tips 86 of wireform 54 is shown in FIG. 5. Needle 78 (not shown) with looped thread 80, which was used to sew the leaflet ends together, is inserted up from leaflets 68 (as shown in dashed lines), through an inner edge of cloth edge 84 as indicated at 87, so that the top surfaces of mating leaflets 68 are secured into contact with wireform 54. The needle is then re-inserted through an outer edge of and from underneath cloth edge 84 as indicated at 88', and a first lock 89, preferably a single lock stitch, is made with thread 80. The locking process can be repeated as indicated at 88" with a second lock 90, preferably a double lock stitch. Finally, the needle can be inserted into the middle of and from underneath cloth edge 84 as indicated at 91 and the thread pulled so that first and second locks 89, 90 are pulled underneath cloth edge 84 and thereby hidden and protected during the remaining fabrication process. The excess thread is then trimmed and discarded. This method is repeated for securing each of the respective pairs of attached, aligned mating leaflet ends of mated leaflets 68a, 68b, 68c of subassembly 52 to the respective commissure tips 86 of wireform 54. Thus, wireform 54 functions as an additional, permanent template for positioning the leaflet commissures in their final position relative to one another. As an added benefit of the present invention, this manufacturing technique further stabilizes the position of the coapting valve leaflets relative to one another prior to attachment of the leaflet cusps to the wireform. Thus, it is possible to attach the entire peripheral leaflet cusp uniformly from the tip of one commissure to the next in order to produce consistent attachment stress along the leaflet edge.

Figure 7:
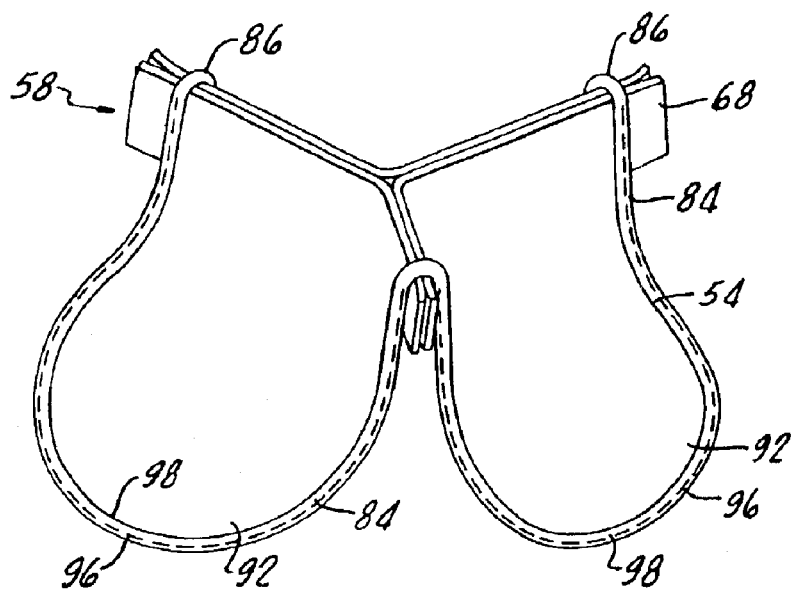
FIG. 7 is a perspective view illustrating the uniform attachment of the perimeter cusps of leaflets to the cloth covered wireform.

Referring now to FIGS. 6 and 7, the next exemplary step for securing the exemplary leaflet subassembly 52 to wireform 54 is to attach peripheral cusps 92 of each of the leaflets 68 to cloth edge 84. In that connection, slip knots 94 (i.e., knots that may be undone) are spaced periodically along wireform 54 to temporarily fit leaflet cusps 92 in position on wireform 54. Three of the slip knots 94 may be made for each leaflet cusp 92, with one at the center of the cusp and two at points of inflection with the commissures, as this helps to uniformly stabilize the cusp in position during attachment to wireform 54.

Figure 8:
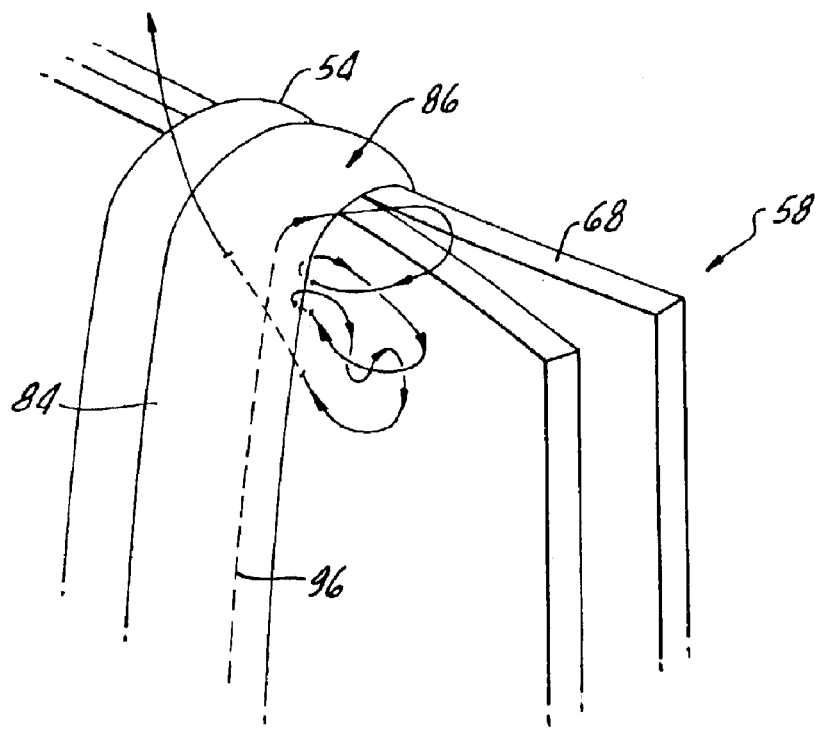
FIG. 8 is an enlarged view of one of the pairs of attached leaflet tabs of FIG. 7 illustrating the uniform attachment of the cusps to the wireform commissure tip.

As shown in FIGS. 7 and 8, temporarily secured leaflet cusps 92 then are attached to wireform cloth edge 84, preferably using double-threaded "in-and-out" sutures 96, starting from a center position 98 of each leaflet cusp 92 and running to the tips of each commissure 86. At about one millimeter from the commissure tips 86, the threads are locked, buried and trimmed, preferably as described previously. Thus, unlike prior art tissue valves wherein leaflets are attached individually and the peripheral stitching of the cusps terminates before the tips of the commissures, producing a potential stress point, the method of the present invention produces a novel tissue valve assembly having uniform stitching from commissure tip to commissure tip and consistently aligned coapting leaflet mating edges.

Attachment of the Tissue-Wireform Structural Assembly to a Support Stent

Figure 9:
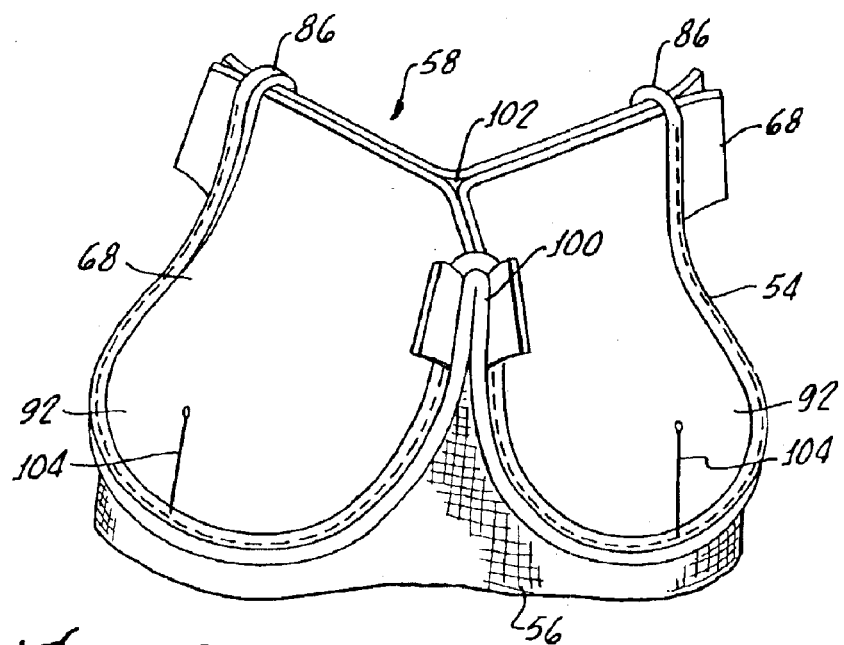
FIG. 9 is a perspective view illustrating the attachment of the exemplary tissue leaflet-wireform structural subassembly to an exemplary stent of the present invention.
Figure 10:
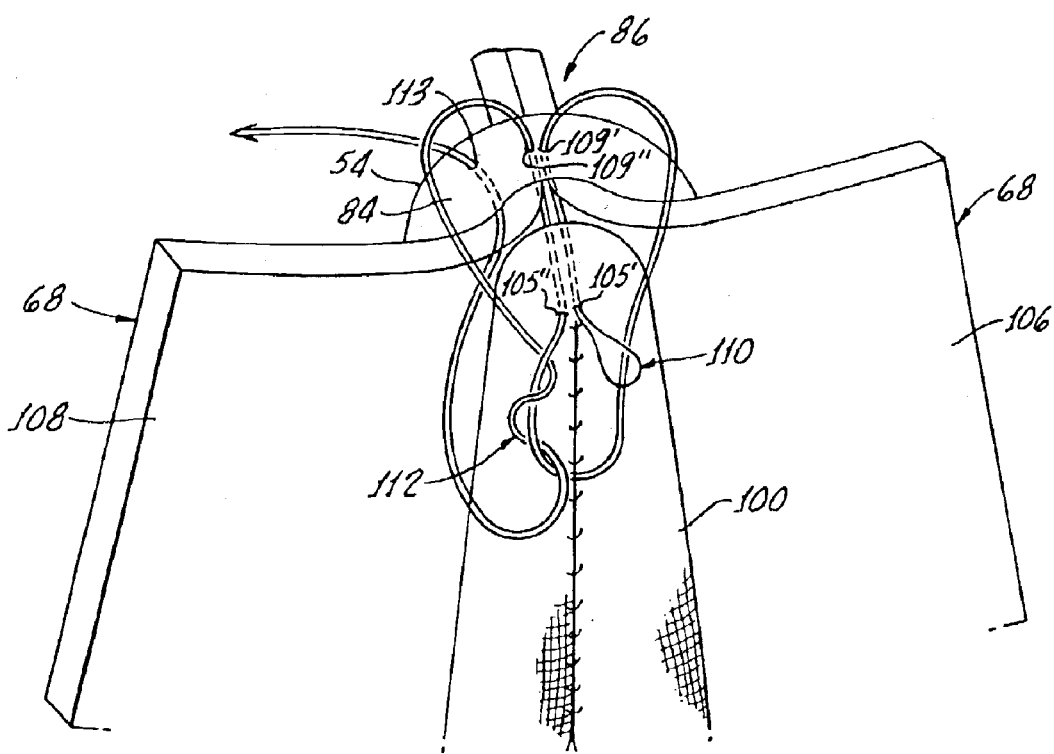
FIG. 10 is an enlarged view of one of the pairs of leaflet tabs of FIG. 9 illustrating a further attachment step of the stent to the wireform at the commissure tip, clamping the leaflet cusps therebetween.
Figure 11:
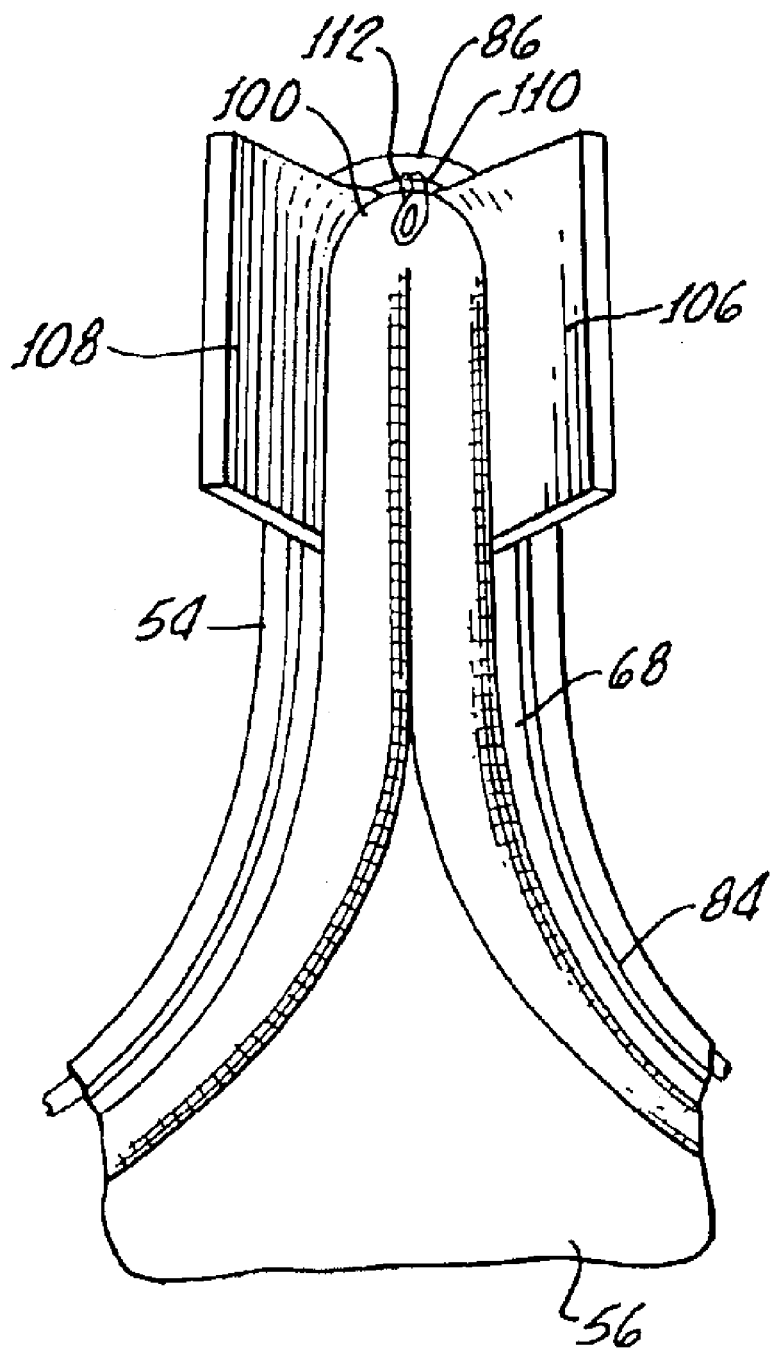
FIG. 11 is an enlarged view of one of the commissure tips of the tissue-wireform structural assembly of FIG. 10 illustrating the clamping of the leaflets by the stent.
Figure 12:
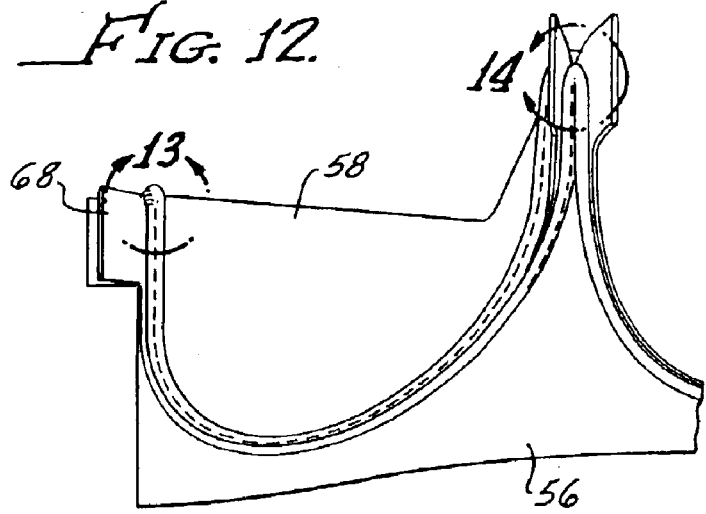
FIG. 12 is a perspective view illustrating a final attachment step of the exemplary tissue-wireform structural assembly to the stent.

For purposes of further explanation, once the assembled tissue-wireform structural assembly, which is identified by reference numeral 58, is produced as discussed above, the assembly 58 is then attached to a support or stent 56. Referring to FIGS. 9, 10, and 11, the tissue-wireform structural assembly 58 is first fitted onto the correspondingly configured stent 56 in a manner that will uniformly clamp the peripheral cusp edges of the leaflets 68 between an upper surface 99 (see FIG. 1) of stent 56 and the lower surface of wireform 54. This assembly technique further distributes stresses and loads of the leaflets 68 and contributes to their functional longevity. Moreover, pre-alignment of the leaflets 68 and attachment to the wireform 54 enables the dimensions of the entire valve 50 to be aligned at once and eliminates the dimensional variation that could occur in prior art valves due to the utilization of separate commissure posts. In particular, stent 56 is dimensioned to mate or seat with the configuration of assembly 58, and assembly 58 is mated to stent 56 such that the lower surface of each commissure tip 86 of wireform 54 mates with the top surface of a corresponding and complementary stent commissure tip 100. Care is taken to ensure that central opening 102 formed by coapting mating leaflets 68 is not distorted while mating tissue-wireform structural assembly 58 to stent 56. Similarly, care is taken to ensure that leaflets 68 are uniformly clamped and remain evenly tensioned throughout this process.

Once wireform assembly 58 is mated to stent 56, a temporary pin 104 can be inserted at the bottom curve of each leaflet cusp 92 to temporarily secure wireform assembly 58 to stent 56. Stent 56 and assembly 58 then are sutured together as shown in FIGS. 10 and 11. Suturing of assembly 58 to stent 56 begins at the tops of the commissure tips 86. In particular, a double-threaded needle (not shown) is inserted through stent commissure tip 100 as indicated at 105', between free tab ends 106, 108 of adjacent pairs of leaflets 68, and through cloth edge 84 of wireform assembly 58 as indicated at 109". The needle is then inserted through the looped thread to form a single lock 110. A double lock 112 is then formed, with the needle being inserted through stent commissure tip at 105" and through cloth edge 84 at 109", substantially in the manner previously discussed so that double lock 112 is able to be pulled underneath cloth edge 84. Excess thread exiting from cloth edge 84 as indicated at 113 may then be trimmed and discarded. The identical procedure may be performed for the remaining commissure tips 86 of the wireform assembly 58. As a result, wireform commissure tips 86 evenly match with stent commissure tips 100.

Figure 13:
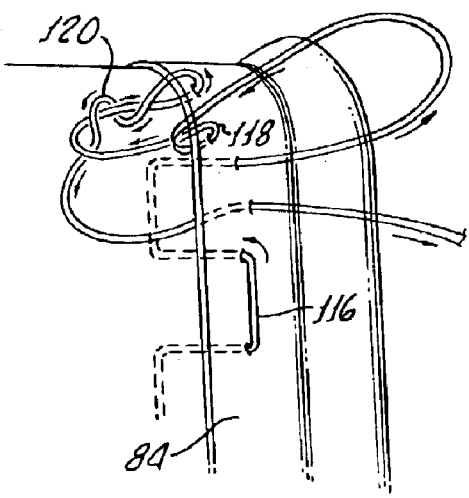
FIG. 13 is an enlarged view taken on circle 13 of FIG. 12 illustrating additional exemplary attachment techniques.
Figure 14:
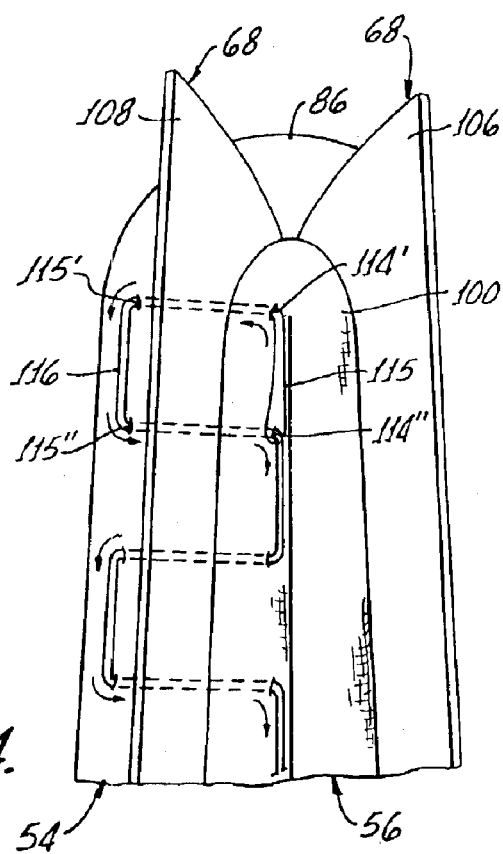
FIG. 14 is an enlarged view taken on circle 14 of FIG. 12 illustrating additional exemplary attachment techniques.

With reference to FIGS. 9 and 12–14, the exemplary attachment procedure can be completed by inserting a double-threaded needle as previously described through stent 56 near the top of stent commissure tip 100 as indicated at 114', through tissue leaflet 68 and through cloth edge 84 of wireform 54 as indicated at 115'. The needle is then re-inserted in a reverse manner through cloth edge at 115", through stent commissure tip 100 at 114" and passed through loop 115 of the double thread. With reference to FIG. 14, the suture is then tightened so that loop 115 is positioned securely and firmly against stent commissure tip 100. In-and-out suturing 116 (see also FIGS. 15 and 16) is then performed along the mating edges of stent 56 and wireform assembly 58 up to the next wireform assembly and stent commissure tips 86, 100. With reference to FIG. 13, at a position near the top of the commissure tip 86, a single lock 118 and a double lock 120 can be formed, and the thread can be buried beneath cloth edge 84 of wireform assembly 58 as described previously. It will be appreciated that the suturing just described may be initiated at any of the stent commissure tips 100 and that the in-and-out suturing 116 may be performed in either a clockwise or a counter-clockwise manner around the periphery of stent 56.

Figure 15:
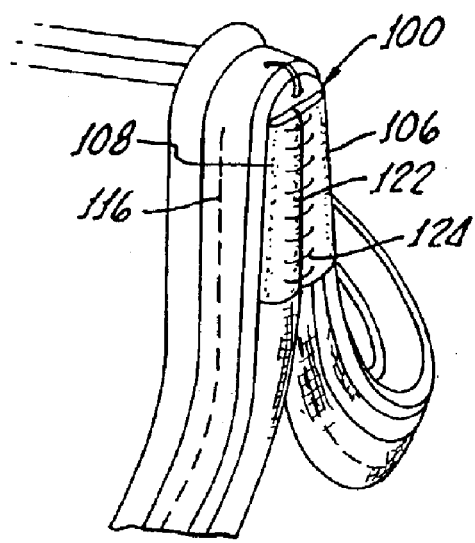
FIG. 15 is a perspective view illustrating an exemplary attachment step of the tissue leaflet tabs at the commissure tip.
Figure 16:
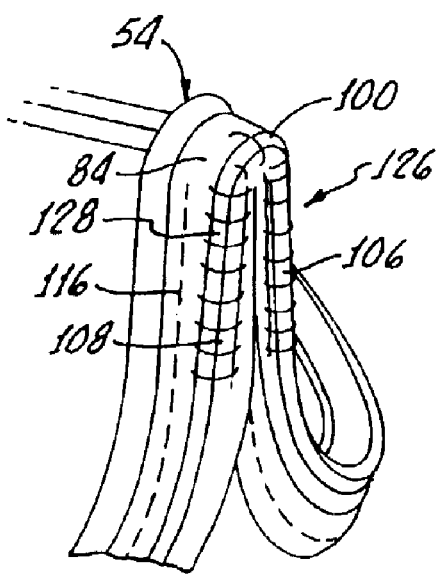
FIG. 16 is a view similar to FIG. 15 illustrating an alternative attachment step.

Upon completion of the in-and-out suturing 116 around the periphery of stent 56, the free tab ends 106, 108 of each pair of tissue leaflets 68 need to be secured to the respective stent commissure tip 100. Referring to FIGS. 15 and 16, two exemplary alternatives are provided to perform this task.

Referring to FIG. 15, a first exemplary alternative is to configure tab ends 106, 108 to form a butt joint 122. In particular, tab ends 106, 108 are trimmed such that, when folded towards each other, the respective end edges of each tab end 106, 108 mate evenly to form, preferably, a straight center line descending vertically from the top of commissure tip 100. The two leaflet tab ends 106, 108 are then stitched together with stitching 124.

Referring to FIG. 16, a second exemplary alternative for securing leaflet tab ends 106, 108 is to configure tab ends 106, 108 to mate evenly to form a flush junction 126 with cloth edge 84 of wireform 54 on either side of commissure tip 100. In particular, leaflet tab ends 106, 108 can be trimmed so that the end edges of each tab 106, 108 are sized to fit flush with cloth edge 84 of the wireform. Leaflet tab ends 106, 108 are then stitched to cloth edge 84 of wireform 54 with stitching 128 as shown. The alternative flush junction 126 so formed provides a somewhat flatter commissure than butt junction 122 of the first alternative does, and, therefore, flush junction 126 may be more desirable when a more compact valve is needed. Both exemplary methods, however, allow even and reliable distribution of the load on the tissue leaflets at the commissures.

Assembly of an Exemplary Stent

From the foregoing description, it will be appreciated that stent 56 is configured to have a structure suitable for mating and supporting wireform assembly 58. In that connection, an exemplary structure of stent 56 will now be described with reference to FIG. 17. Those skilled in the art will appreciate that the exemplary stent described herein is a multi-piece construction. However, it is contemplated as being within the scope of the present invention to provide a single-piece stent. However, the multi-piece stent assembly illustrated may make it easier to engineer or fine tune the radial stability of the stent while maintaining desirable axial flexibility of the commissure posts. The first step in the assembly of exemplary stent 56 is to fabricate an inner support member 130 and an outer support member 132, which, when mated together, generally form the shape of stent 56 which ultimately conforms to the configuration of wireform assembly 58. In the exemplary embodiments inner support member 130 is configured with three upstanding posts 134 that serve as the support structures for the stent commissure tips 100. Outer support member 132 also may include posts 136 that correspond to the posts 134 of the inner support member 130. However, posts 136 are truncated and therefore do not match the height of posts 134 on inner member 130. The inner and outer support members 130, 132 may be fabricated from a metal or plastic material depending on the desired characteristics of valve 50.

Disposed on inner support member 130 are a plurality of sewing holes 138 along the periphery of member 130 and on the posts 134. The outer support member 132 includes at least one sewing hole 139 on each of its truncated posts 136 that correspond with respective ones of the sewing holes 138 on each post 134 of the inner member 130. The inner diameter of outer support member 132 is sized to form a slip fit with the outer diameter of inner support member 130.

Inner support member 130 is placed within outer support member 132 such that sewing holes 139 of outer support member 132 align with sewing holes 138 on the respective posts 134 of inner member 130. The two members are then sewn together by inserting a double-threaded needle as described previously through the aligned holes 138, 139. As shown in FIG. 18, thread 140 inserted through each of the aligned holes 138, 139 is then passed through end loop 142 and tightened. The thread may then be locked using, for example, a slip knot (not shown), which is a knot that may slide along the thread to abut the support members. Accordingly, posts 134 of inner support member 130 flex to a greater extent from base portions thereof to tops thereof, and outer support member 132 augments the radial stability of inner support member 130, with the truncated posts 136 providing rigidity to base portions of posts 134 of inner support member 130.

Referring now to FIG. 19, once the inner and outer support members 130, 132 are sewn together, a covering cloth 144, preferably made from woven polyester, is cut and formed into a cylindrical tube for covering the-combined support members 130, 132. Those skilled in the art will appreciate that the covering cloth is equally applicable to single-piece stent assemblies. Covering cloth 144 includes two crease lines 146, 148, the first of which, 146, is formed from folding an edge of cloth 144 to form a fold which receives posts 134 of inner support member 130. There is approximately 1 mm to 1.5 mm between first crease line 146 and a top edge 149 (see FIGS. 17 and 18) of each post 134 in the exemplary embodiment. Second crease line 148 is located such that it corresponds to a lower edge 150 (see FIG. 18) of combined support members 130, 132.

Figure 20:
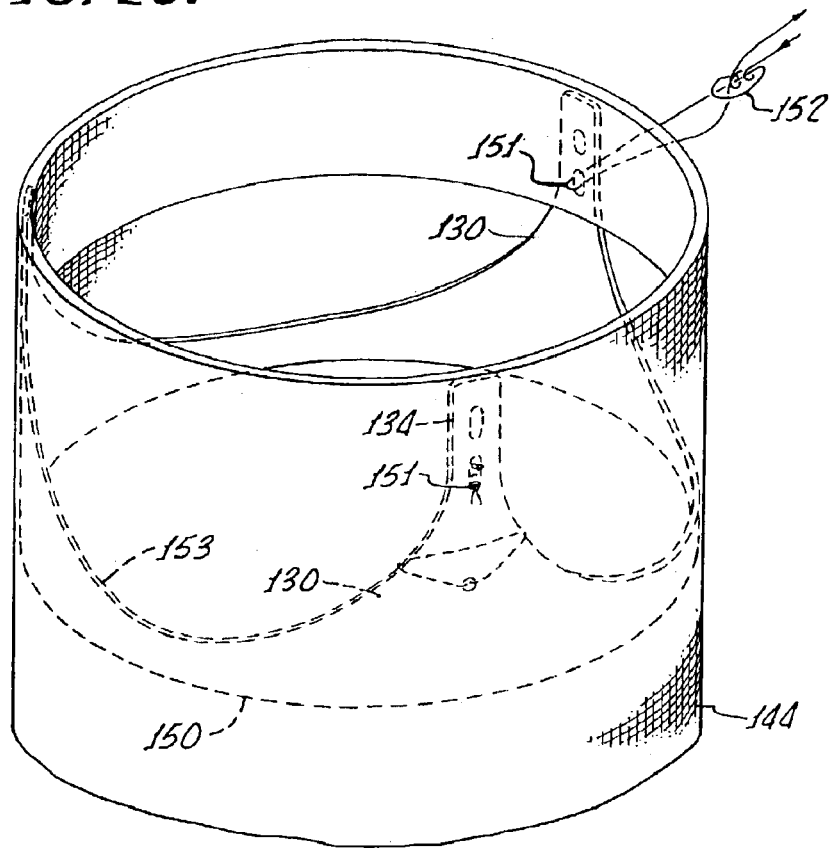
FIG. 20 is an enlarged view of the top of FIG. 19 illustrating additional steps in the attachment of the cloth to the stent components.

Referring now to FIG. 20, to secure covering cloth 144 to support members 130, 132, a threaded needle may be inserted through, cloth 144, through a hole 151 of one of inner member posts 134, through the second layer of cloth 144 and then back through cloth 144 through the same hole 151 and through cloth 144. The needle then can be passed through a loop to form a first lock 152. This threading step may be performed up to two more times. The excess thread is then trimmed and discarded. The same procedure can be followed for each of the three posts 134 on inner support member 130.

Figure 21:
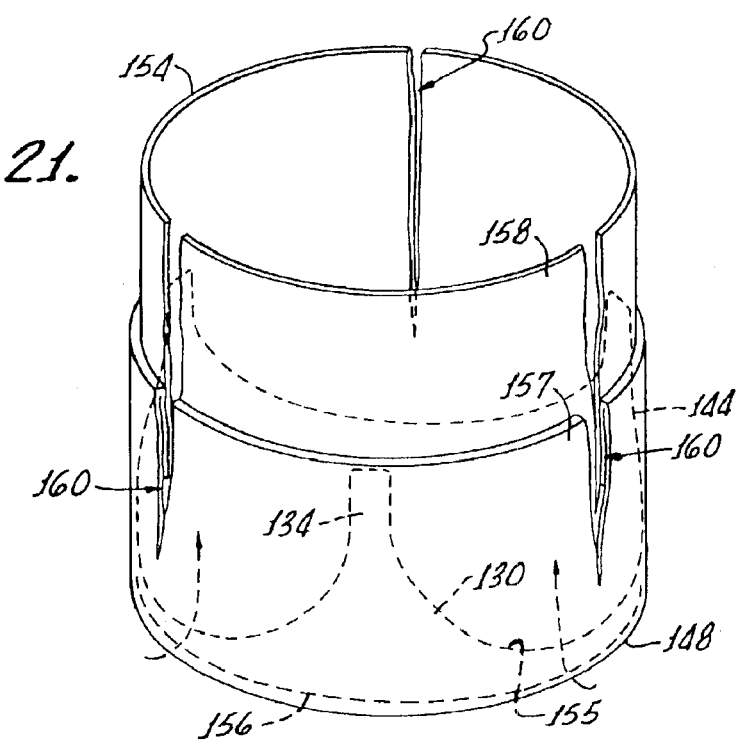
FIG. 21 is a perspective view illustrating additional steps of fabricating sewing tabs for attaching the cloth to the stent components.

Then, as shown in FIG. 21, the next exemplary step involves stitching covering cloth 144 to inner and outer support members 130, 132 along an upper edge 137 of inner support member 130. First, lower edge 154 of cloth 144 can be folded into the interior of support members 130, 132 along crease line 148 such that second crease line 148 defines the lower end or bottom of the support member structure. This fold results in dual-layered cloth 144 (including outer and inner cloth layers 156, 158) enveloping support members 130, 132. Then, using a single threaded needle, the layered cloth is stitched together at 155 along the curvature of the upper edge 153 of support members 130, 132. The stitching 155 is preferably backstitching, which is accomplished by inserting the needle a stitch length, for example, to the right and bringing it up an equal distance to the left. However, the stitching 155 does not extend to the tops 149 of posts 134, leaving a space of approximately 1 mm between the top 149 of post 134 and the stitching 155. After stitching the upper edge 153 of support members 130, 132, the cloth 144 then can be stitched in a similar manner at 156 along the lower edge 150 of support members 130, 132. The last stitch is then locked by tying a slip knot, which may be performed up to three times to lock the stitching securely in place.

Referring now to FIGS. 21–26, cloth 144 as now attached to support members 130, 132 is trimmed to conform to the shape of support members 130, 132 and, if desired, to provide a gasket-like sewing edge. To accomplish this, outer cloth layer 157 can be sliced downwardly from a top edge thereof to a distance approximately 5 mm to 6 mm above the top edge 153 of inner support member 130. In a similar manner, inner cloth layer 158 can be sliced downwardly from a top edge thereof to a distance approximately 2 mm to 3 mm above the bottom of the slice in outer cloth layer 157. The slices are made at a location midway between adjacent posts 134 of inner member 130 and are intended to align with one another in the downward direction, as indicated at 160.

Next, outer cloth layer 157 can be trimmed along the upper edge 153 of inner support member 130, starting at the bottom of the slice formed in outer cloth layer 157. In this exemplary embodiment of the present invention the trimming is performed in a manner such that the contour of the cloth 144 extends a distance of approximately 4 mm to 5 mm above the lower curved portions of the upper edge 153 of support member 130, a distance of approximately 2 mm to 3 mm above portions of support member 130 in the areas at or near the base of posts 134 of support member 130 and a distance of about 0.5 mm to 2 mm above the tops 149 of posts 134 of support member 130.

As shown in FIG. 22, inner cloth layer 158 is then folded over the tops 149 of posts 134 of inner member 130 and is anchored to posts 134 with a threaded needle stitched through sewing hole 151 in posts 134 in the manner previously described with respect to the upper folded section of cloth 144. However, after these locking stitches are executed, the needle is passed under the cloth so as to exit from the top of post 134.

Next, a series of trimming operations can be performed. Referring to FIGS. 22 and 23, a folded portion 162 of inner cloth layer 158 is trimmed around the entire circumference of the cloth so that lower edge 164 of folded portion 162 is approximately 1 mm to 1.5 mm from the stitch in hole 151 of post 134. A folded portion 168 of outer cloth layer 157 is folded over the tops 149 of post 134 of inner support member 130. Folded portion 162 of the inner cloth layer 158 is further trimmed so that its remaining edges are flush with the edges of the previously trimmed inner cloth layer 158. With regard to the non-folded portion of inner cloth layer 158, this layer is trimmed in a manner such that its edges extend approximately 2 mm beyond the edges of the previously trimmed outer cloth layer 157. The 2 mm extension of the inner cloth layer 158 beyond the outer cloth layer 157 provides the material desired to form a seating and attachment or sewing surface on the stent.

Each of the trimming operations is performed starting from the central area between posts 134 of inner support member 130 to the tops 149 of posts 134. The arrangements of inner cloth layer 158, outer cloth fold 168, outer cloth layer 157 and inner cloth fold 162 are shown in the enlarged cross-section of FIG. 23.

The remaining exemplary step to complete the assembly of the stent 56 is to fold and suture the cloth layers to form a sewing edge 169 around the stent 56. Referring to FIG. 24, inner cloth layer 158 is folded around post 134 and stitched so as to enclose post 134. More specifically, the thread previously inserted through the top of post 134 when connecting folded outer cloth layer 157 through sewing hole 151 is now used to create first and second locks 172 on the top of post 134 so as to hold inner cloth layer 158 in place on the top of post 134. A wipstitch 174 may then be utilized to further secure exemplary inner cloth layer 158 downwardly around post 134 approximately 8 mm from the top of post 134. When the bottom of the post 134 is reached, first and second locks are formed, and the thread is trimmed and discarded. The above-described stitching operation is performed for each of the three posts 134. However, for the last of the posts 134 to be stitched, instead of trimming the thread after forming the first and second locks 172, untrimmed thread 176 can be used for performing the stitching of the cloth along the remaining edges of support members 130, 132 between posts 134.

In that connection, with reference to FIGS. 25 and 26, inner cloth layer 158 is folded over the outer cloth layer 157, and an alternating stitching is applied to hold the folded layers in place on the support members and thereby to form the sewing edge 169 on the stent. After completing the stitching around the remaining portions of the support members 130, 132, a first and second lock stitch can be formed with the thread, and the excess thread is trimmed and discarded to complete the assembled stent 56.

Assembly of an Exemplary Suture Ring

Where valve 50 is intended for use in the replacement of a native heart valve, a soft suture ring 60 is contemplated for use in completing the valve structure. For example, referring to FIG. 27, an exemplary ring washer 180 is provided which is preferably made from non-woven polyester, such as a material sold under the trade name REMAY manufactured by Remay, Inc., Old Hickory, Tenn. Also provided is a silicone sponge waffle annulus 182 for mating with washer 180. In that connection, annulus 182 is configured to have a walled lip 184 configured to be disposed along the inner circumference 185 of washer 180. Lip 184 is contoured to include three depressions 186 that correspond with the lower curved surfaces between each commissure on valve 50. Washer 180 mounts on waffle annulus 182 such that washer 180 surrounds the walled lip 184. This produces a soft, relatively flexible, yet stable suture ring internal structure which, when covered with cloth as discussed below, functions as a compliant, stitchable interface between the natural tissues of the heart and the prosthetic tissue valve 50.

Figure 28:
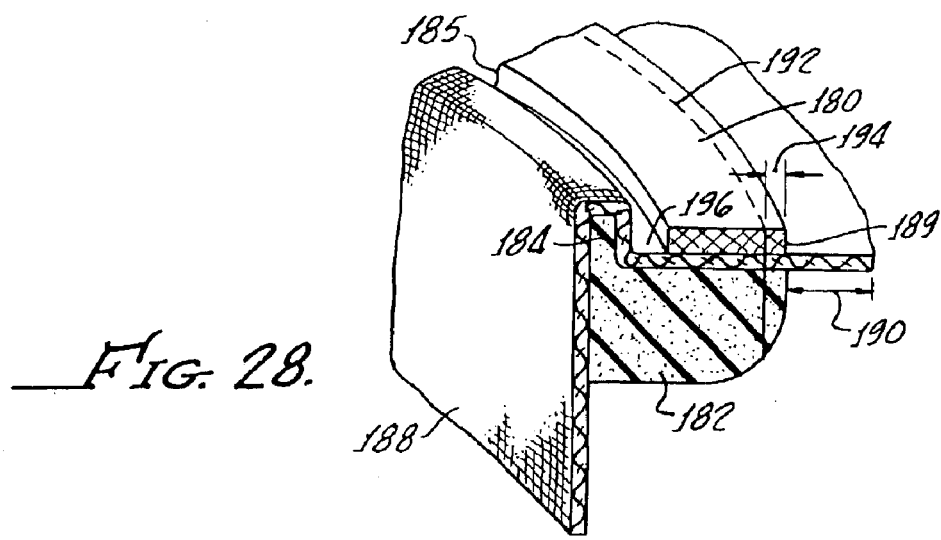
FIG. 28 is an enlarged cross-sectional view illustrating aspects of the fabrication of the exemplary suture ring.
Figure 29:
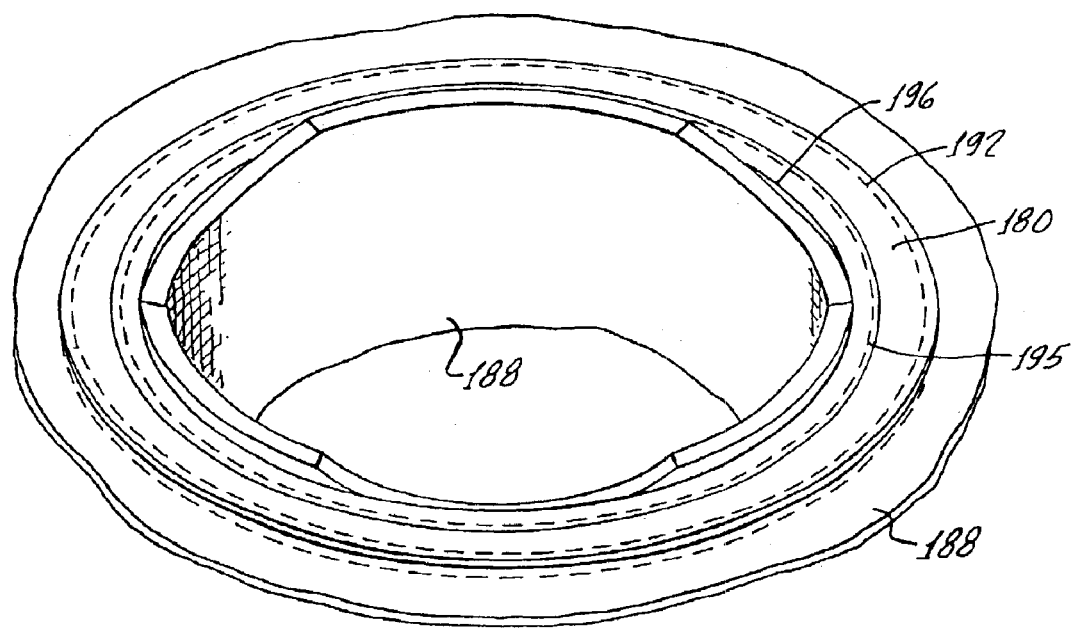
FIG. 29 is a perspective view illustrating additional features of the exemplary suture ring assembly.

As shown in FIG. 28, before mounting washer 180 on waffle annulus 182, a cloth 188 is positioned around washer 180 to extend from the inner circumference 185 to the outer circumference 189. Washer 180 is then mounted on waffle annulus 182 such that cloth 188 is sandwiched between waffle annulus 182 and washer 180. Cloth 188 is placed to extend a distance 190 of approximately 3 mm to 5 mm beyond the outer circumferential edge 189 of washer 180, as shown in FIG. 28. Washer 180, cloth 188 and waffle annulus 182 are then sewn together using, for example, in-and-out suturing 192 around the circumference of washer 180. The exemplary suturing is preferably placed a distance 194 of approximately 1 mm from the outer circumferential edge 189 of washer 180. If desired, a second suture line (not shown) may be added at the same location as the first suture line, with each stitch of the second suture line placed between the stitches of the first suture line. The resulting suture 192 then appears as a continuous line of stitching. Additionally, as shown in FIG. 29, to further secure cloth 188 and waffle annulus 182 together, back stitching 195 may be applied in the space between the walled lip 184 of annulus 182 and washer 180, which space is indicated at 196 in FIG. 28.

Referring now to FIG. 30, cloth 188 can be attached to depressions 186 of the structural assembly of washer 180 and waffle annulus 182 with, for example, a single-threaded needle inserted at one corner 198 of depression 186 (through cloth 188 and annulus 182) and then with a double slip knot to secure the thread at corner 198. In-and-out stitching 200 can be then used to secure cloth 188 to the contour of depression 186. The same method can be followed for each depression 186. The excess cloth is then trimmed to the outer edge of washer 180 as indicated at 201.

With additional reference to FIG. 31, an outer portion 202 of cloth 188 then can be folded around the external surfaces of washer 180 and tucked under washer 180 between washer 180 and waffle annulus 182. Because of annulus 182 is pliant, annulus 182 deforms and accommodates the outer portion 202 of cloth 188. Using a single-threaded needle, an alternating stitch 204 can be used to secure folded cloth 188 underneath washer 180. After completing the stitching of the entire circumference of washer 180, a double knot can be formed to secure the stitching, yielding a finished suture ring.

Attachment of the Suture Ring to the Exemplary Valve

Figure 32:
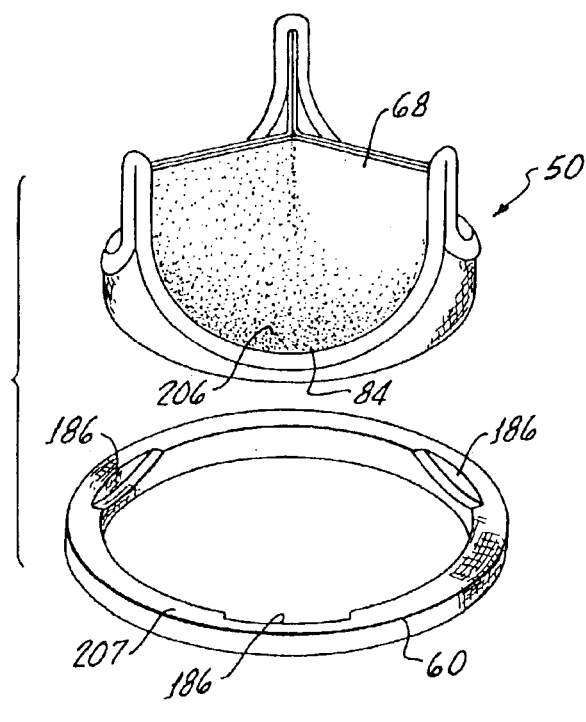
FIG. 32 is an exploded perspective view illustrating positioning and assembly of a suture ring and leaflet subassembly configuration.
Figure 33:
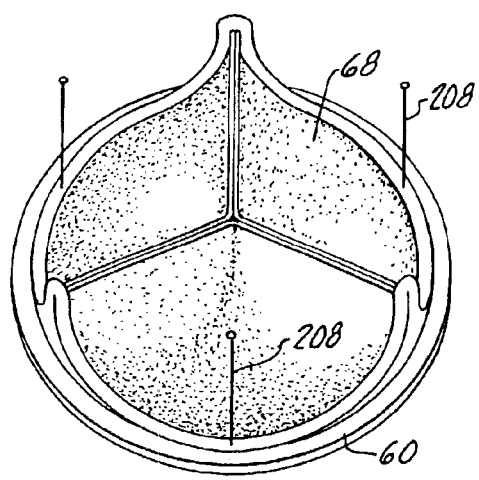
FIG. 33 is a top perspective view illustrating additional suture ring leaflet subassembly attachment steps.

Referring to FIGS. 32 and 33, to attach suture ring 60 or an alternative structure such as flange 62 (see FIG. 1) to valve 50, depressions 186 of suture ring 60 are aligned with the descending peripheral cusps 206 of valve 50 and then mated together. More specifically, valve 50 is placed on suture ring 60 such that cloth edge 84 of the wireform 58 on the lower-most portion of each cusp on valve 50 is substantially flush with a top surface of suture ring 60 at corresponding depressions 186. Care is taken with the placement such that kinking or wrinkling of tissue leaflets 68 is avoided. Valve 50 can be temporarily pinned in place on suture ring 60 with needles 208 to facilitate this procedure.

Figure 34:
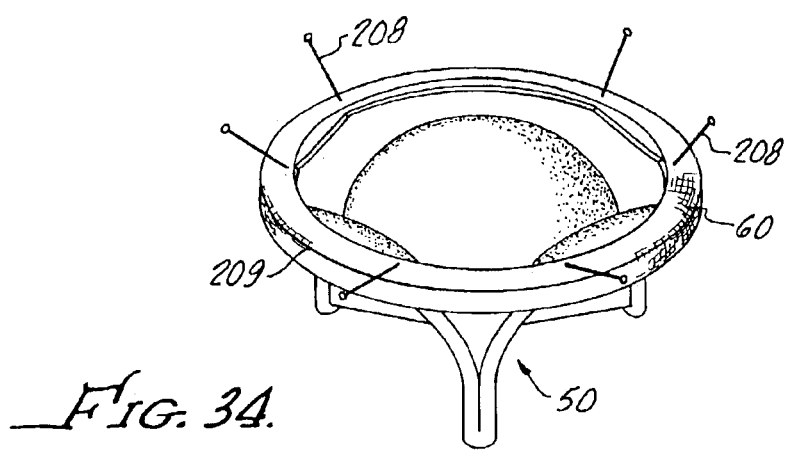
FIG. 34 is a bottom perspective view illustrating further exemplary suture ring attachment steps.

As shown in FIG. 34, the assembly of pinned valve 50 and suture ring 60 can be flipped over, and suture ring 60 can be stitched to valve 50 along mating edges 209 of ring 60 and valve 50. More specifically, in the exemplary embodiment a single threaded needle can be used to sew suture ring 60 to the cloth of the stent structure. To facilitate the stitching step, the pieces are held temporarily, yet securely in place with additional needles 208. The opposite side of ring 60 and valve 50 can be sewn together in a similar manner.

Attachment of Valve to Outflow Conduit

Referring now to FIGS. 35–37, in certain applications, it may be desirable to attach valve 50 to an outflow conduit such as that shown at 66. For example, in some patients requiring replacement of the aortic valve, a portion of the aorta itself may be damaged or diseased such that it needs replacement as well. Accordingly, consistent with the teachings of the present invention, the adaptable tissue valve structure can be modified to include an outflow conduit 66 that will function to replace the damaged aorta. Alternatively, in some intended mechanical pumping applications the adaptable tissue valve of the present invention may be provided with an outflow conduit to facilitate interfacing with the mechanical pumping structure. In either alternative, this can be accomplished as shown in FIGS. 35 and 36 where an outflow conduit 66 may be attached to wireform 54 at the time that the tissue leaflets 68 are being secured. In particular, referring to FIG. 36, conduit 66 may be secured on a side of wireform 54 opposite to tissue leaflets 68 by, for example, stitching. Alternatively, as shown in FIG. 37, conduit 66 may be stitched and secured to wireform 54 on the same side as tissue leaflets 68, or sandwiched therebetween. A third option is to simply secure conduit 66 to the periphery of the finished valve (not shown) as a subsequent sewing step. The valve 50 may be attached to an outflow conduit either with or without a sinus.

Alternative Configurations for Inflow Side of Valve

Figure 38:
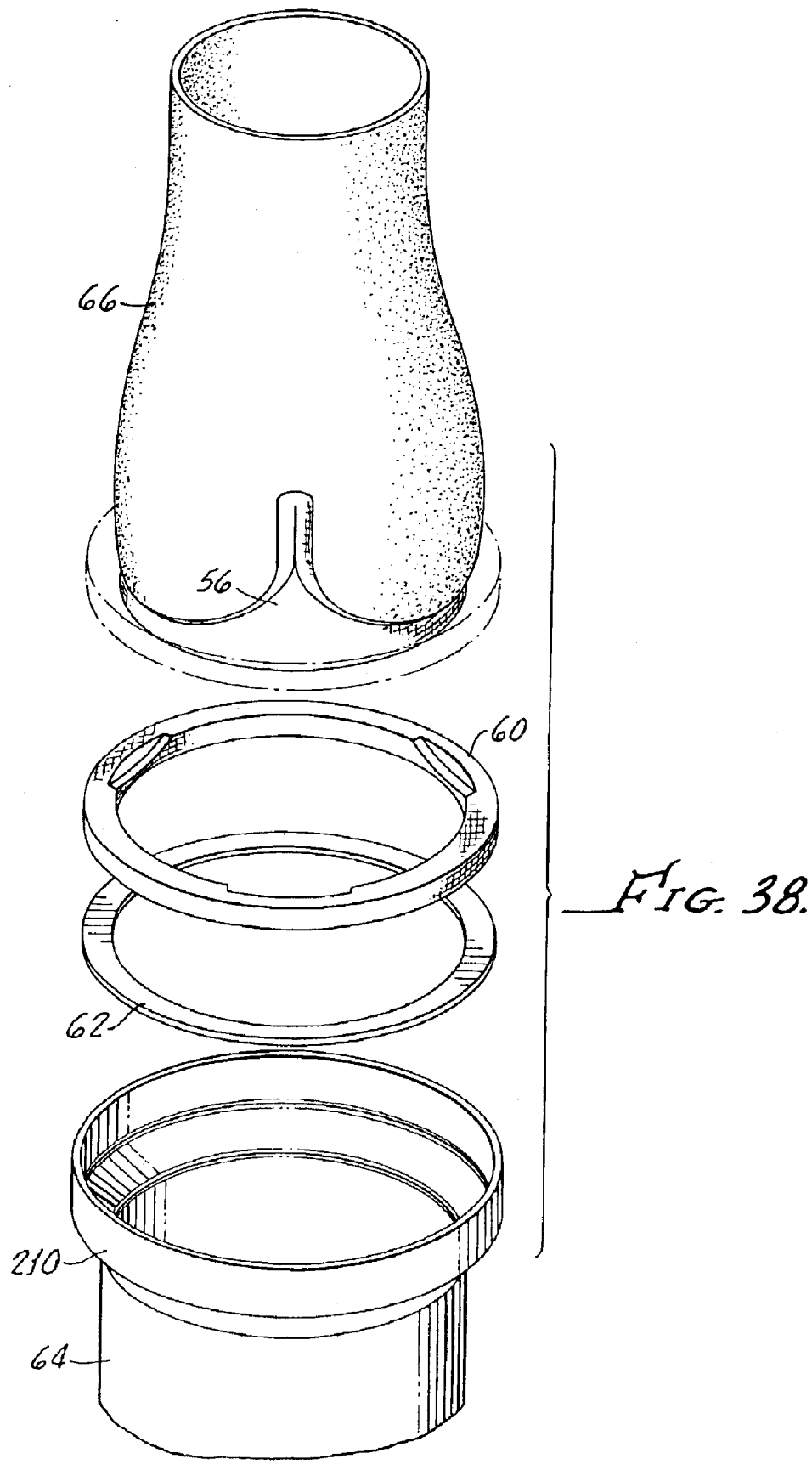
FIG. 38 is an exploded perspective view illustrating additional valve attachment alternatives of the present invention.

FIG. 38 illustrates additional exemplary alternative options available for modification and attachment of valve 50. For example, as discussed above, when it is desired to use valve 50 as a conduit valve, suture ring 60 may be attached to valve 50 as previously described. Alternatively, in applications such as artificial hearts or left ventricular assist devices (LVADs), suture ring 60 is not necessarily required; hence, the lower end of stent 56 may be attached to flange 62 for use in mounting the valve in the artificial heart or LVAD.

Yet a further alternative adaptation involves those applications where an inflow conduit 64 is desired. In such applications, inflow conduit 64 may be attached directly to stent 56 of valve 50. More specifically, inflow conduit 64 may be configured to have a stepped circumference 210 that snugly mates with the outer periphery (or, alternatively, the inner periphery) of stent 56 and which can be sewn thereto. In this configuration, for example, in an artificial heart or an LVAD application, suture ring 60 could be attached to inflow conduit 64 rather than to valve 50.

Conclusion

In view of the foregoing description of exemplary embodiments of valve 50 and the components thereof, the present invention satisfies the need for improved tissue-type prosthetic heart valves in which stress is reduced on valve leaflets 68 while desirable structural and functional features are maintained. Additionally, valve 50 is adaptable for use in a variety of positions within the natural heart or in mechanical pumps. Further, valve 50 is simpler and easier to manufacture in a more consistent manner than existing valves.

The standardized leaflet structure subassembly 52 of the present invention can be modified readily to adapt to different intended applications. Of equal importance, leaflet subassembly 52 uniformly distributes tensile loads along the entire periphery of leaflet cusps 92, reducing stress points and significantly improving the long-term functionality of valve 50. As an added benefit of the present invention, the stability and adaptability of the tissue valve subassembly is achieved through simplified manufacturing processes utilizing fewer steps and subassemblies. This manufacturing protocol can be incorporated into branched, adaptable manufacturing techniques for the production of tissue heart valves having a variety of end uses. Further, these improved construction techniques expedite the overall manufacturing process and improve the consistency of valve 50 while simultaneously reducing the need for post-assembly fine tuning and quality-control procedures.

The plurality of tissue leaflets 68 being attached together as described form the dimensionally stable and dimensionally consistent coapting leaflet subassembly 52. Further, sutures 96 used to attach cusps 92 to wireform 54 act like similarly aligned staples, all of which equally take the loading force acting along the entire periphery of cusp 92 of each pre-aligned, coapting leaflet 68. The resulting tissue-wireform structural assembly 58 reduces stress and potential fatigue at the leaflet suture interface by distributing stress evenly over the entire leaflet cusp 92 from commissure to commissure. Further, tissue-wireform structural assembly 58 may be attached to cloth-covered stent 56 without disturbing leaflets 68 or disturbing their relative alignment and the resultant coaptation of their mating edges.

Stent 56 as fabricated according to the present invention provides evenly distributed support and dimensional stability for each leaflet 68 of the valve structure 50 from commissure to commissure. This assembly methodology allows the evenly sutured tissue of leaflet cusps 92 to be sandwiched between wireform 54 and stent 56 and to thereby further distribute the loading forces more evenly around the attachment site. Because leaflets 68 experience lower, more evenly distributed stresses during operation, leaflets 68 are less likely to experience distortion in use. Thus, a more stable, long lived, functional closure or coaptation of leaflets 68 is provided by this even distribution of attachment forces.

Furthermore, for each key area of stent 56, the flexibility can be optimized or customized. If desired, the coapting tissue leaflet commissures 86 can be made more or less flexible to allow for more or less deflection to relieve stresses on the tissue at closing or to fine tune the operation of valve 50. Similarly, the base radial stiffness of the overall valve structure can be increased or decreased to preserve the roundness and shape of valve 50. Unlike a rigid mechanical valve, stent 56 does not act as a rigid heart valve structure but as a radially stable, yet axially flexible support. A rigid structure is unnecessary by utilizing the teachings of the present invention because leaflets 68 are dimensionally pre-aligned along their mutually coapting mating or sealing edges 70 prior to being directly attached to cloth-covered wireform 54. As a result, the entire sealing aspect of valve 50 can be aligned in three dimensions at once without the variability previously experienced in the construction of prior art tissue-type valves. In addition to eliminating the need for post-assembly adjustment, this pre-alignment provides for consistency and simplicity in the manufacture of valve 50. Further, wireform 54 functions as a template for suturing leaflet cusps 92 to the valve subassembly with uniform stitching from commissure tip 86 to commissure tip 86. This produces a dimensionally consistent structure that can interface with stent 56 in a previously unobtainable uniform manner. The consistent dimensional integrity of leaflet wireform subassembly 58 enables stent 56 to function as a stress relieving support clamp which further secures leaflet cusps 92 in valve 50 to provide an added degree of stability and stress distribution. If desired, providing the top 99 of the stent 56 with a single or double fold of covering cloth 144 provides the stent lip with a deformable cloth seat that assists in the distribution of load around leaflet cusps 92 and simplifies sewing stent 56 to tissue-wireform structural subassembly 58. Those skilled in the art will appreciate that attaching stent 56 to tissue-wireform structural subassembly 58 functions to stabilize the projecting commissure posts of the valve subassembly without stiffening their desirable axial flexibility. This novel construction technique eliminates the need for separate commissure posts at the tissue leaflet commissures and also eliminates multiple tissue and cloth layers at wireform commissures 86 which adds to uniformity and consistency in valve production and eliminates assembly steps. As a result, valve manufacture is not only improved, but simplified and expedited as well.

Stent 56 also functions as an adaptable structural interface, allowing the tissue-wireform-stent structural subassembly to be attached to a variety of additional structures dependent upon intended valve placement and operating environments, including soft suture ring 60, mechanical flange 62, inflow conduit 64, and outflow conduit 66. Unlike prior art tissue heart valves, the present invention provides this flexibility and adaptability of use because key valve components can be standardized for different types of valves or valve applications. This manufacturing and structural consistency also improves quality control and provides repeatability and consistency in the formation of the valves. It also simplifies final assembly that in turn provides for increased production rates without sacrificing consistent product quality.

As part of the flexibility of the present invention, stent 56 may be designed to be adaptable so that different ways of attaching valve 50 to various intended applications can be accommodated. The novel construction that allows for this universal application results from stent 56 providing a complete uniform support to the dimensionally stable, pre-aligned wireform/leaflet subassembly 58. Because of this adaptability, valve 50 can function in a variety of applications, including that of a temporary heart valve prosthesis within a circulatory support system using a relatively rigid flange or a conduit assembly rather than a standard soft sewing ring. Alternatively, valve 50 can function as a prosthetic valve having a soft, scallop-shaped sewing ring for aortic positioning or a soft flat sewing ring for mitral positioning, or as a conduit valve by incorporating proximal and distal conduits attached on both the inflow and outflow valve ends. The outflow conduit can have a sinus shape to improve blood flow if desired. Within an artificial heart system, valve 50 mimics the hemodynamic pumping action of the heart while sustaining the patient until a donor heart is located and successfully transplanted. In this application, both blood inflow and outflow functions can be accommodated by valve 50.

From the foregoing detailed description, it will be evident that there are a number of changes, adaptations and modifications of the present invention which come within the province of those skilled in the art. However, it is intended that all such variations not departing from the spirit of the invention be considered as within the scope thereof as limited solely by the claims appended hereto.

What is claimed is:

1. A prosthetic heart valve comprising:

a valve including a plurality of flexible leaflets whose outer edges attach to a support structure having a plurality of axially projecting commissures terminating in tips, the commissures being separated by arcuate cusps, the commissures and tips defining a generally sinusoidal line with the commissures extending in the outflow direction and the cusps extending in the inflow direction; and a suture ring fixedly disposed upon an inflow end of the valve comprising a suturable annulus having upwardly opening depressions on an internal circumference corresponding in number to the number of cusps of the support structure, wherein the suture ring has a bore sized to receive the cusps in the depressions.

2. The valve of claim 1, wherein the suture ring comprises a sponge waffle covered with cloth.

3. The valve of claim 2, wherein the sponge waffle comprises an upwardly facing outer ledge and an inner lip projecting up from the ledge in which the depressions are formed.

4. The valve of claim 3, further comprising a ring washer sized to closely surround the lip and rest on the ledge.

5. The valve of claim 4, further comprising a single cloth covering surrounding the sponge waffle, and folded around external surfaces of the ring washer and tucked between the ring washer and the sponge waffle.

6. The valve of claim 4, further comprising a cloth covering surrounding the sponge waffle and extending between the ring washer and the sponge waffle.

7. The valve of claim 1, wherein the suture ring comprises a sponge waffle in combination with a non-woven polyester ring washer, and a cloth covering, to form a stable suture ring which functions as a compliant, stitchable interface between the natural tissues of the heart and the prosthetic heart valve.

8. The valve of claim 1, wherein the suture ring comprises a compliant internal structure and a cloth covering, and the cloth covering is secured to the contour of the depressions.

9. The valve of claim 1, wherein the plurality of flexible leaflets includes:

a tissue leaflet subassembly attached within the support stucture and formed by a plurality of substantially identical tissue leaflets, each of the leaflets having a coapting mating edge having opposing ends and a generally arcuate peripheral cusp extending therebetween coupled to one of the support stucture cusps.

10. The valve of claim 1, wherein the support structure comprises:

an annular wireform having a plurality of axially projecting outflow commissures terminating in arcuate tips, the commissures being separated by arcuate cusps having a substantially larger radius of curvature than the tips, the commissures and tips being formed in a sinusoidal configuration with the commissures extending in the opposite axial direction from the cusps so that each commissure is defined by spaced apart portions of the wireform in adjacent cusps joined by one of the tips.

11. The valve of claim 10, wherein the support structure further comprises:

a generally cylindrical support stent having an upper edge defining a plurality of upwardly projecting flexible posts and arcs therebetween adapted to conform and attach to the wireform commissures and arcuate cusps; and a cloth covering sewn over the stent such that the cloth covering encloses the support structure and substantially conforms to the shape of the support structure.

12. The stent of claim 11 wherein the cloth covering comprises a sewing edge formed by folding and stitching together portions of the cloth covering at the upper edge of the support structure.

13. The stent of claim 12, wherein the sewing edge extends along the entire upper edge, including over the flexible posts.

* * * * *

UNITED STATES PATENT AND TRADEMARK OFFICE
CERTIFICATE OF CORRECTION

PATENT NO.        : 6,945,997 B2
APPLICATION NO.   : 10/412160
DATED             : September 20, 2005
INVENTOR(S)       : Huynh et al.

Page 1 of 1

It is certified that error appears in the above-identified patent and that said Letters Patent is hereby corrected as shown below:

In the Claims,

In Claim 1, Column 18, lines 26-27, cancel the text "the commissures and tips defining a generally sinusoidal line," and insert the following: --the commissures and cusps defining a generally sinusoidal line--

In Claim 10, Column 19, lines 8-9, cancel the text "the commissures and tips being formed in a sinusoidal configuration," and insert the following: --"the commissures and cusps being formed in a sinusoidal configuration--

Signed and Sealed this
Tenth Day of February, 2015

Michelle K. Lee
*Deputy Director of the United States Patent and Trademark Office*